(12) United States Patent
Kaas et al.

(10) Patent No.: US 12,157,885 B2
(45) Date of Patent: Dec. 3, 2024

(54) METHODS OF SCREENING USING BARCODED LIBRARIES

(71) Applicants: President and Fellows of Harvard College, Cambridge, MA (US); The General Hospital Corporation, Boston, MA (US)

(72) Inventors: Christian Schroeder Kaas, Boston, MA (US); Alejandro Chavez, New York, NY (US)

(73) Assignees: President and Fellows of Harvard College, Cambridge, MA (US); The General Hospital Corporation, Boston, MA (US)

( * ) Notice: Subject to any disclaimer, the term of this patent is extended or adjusted under 35 U.S.C. 154(b) by 1729 days.

(21) Appl. No.: 16/315,230

(22) PCT Filed: Jul. 6, 2017

(86) PCT No.: PCT/US2017/040853
§ 371 (c)(1),
(2) Date: Jan. 4, 2019

(87) PCT Pub. No.: WO2018/009628
PCT Pub. Date: Jan. 11, 2018

(65) Prior Publication Data
US 2019/0161751 A1  May 30, 2019

Related U.S. Application Data

(60) Provisional application No. 62/358,878, filed on Jul. 6, 2016.

(51) Int. Cl.
| | | |
|---|---|---|
| C12N 15/10 | (2006.01) | |
| A61K 31/7088 | (2006.01) | |
| A61K 45/00 | (2006.01) | |
| C12N 9/22 | (2006.01) | |
| C12N 15/11 | (2006.01) | |
| C12N 15/81 | (2006.01) | |
| C12N 15/90 | (2006.01) | |
| C12Q 1/68 | (2018.01) | |
| C40B 30/06 | (2006.01) | |
| C40B 40/08 | (2006.01) | |

(52) U.S. Cl.
CPC ...... *C12N 15/1075* (2013.01); *A61K 31/7088* (2013.01); *A61K 45/00* (2013.01); *C12N 9/22* (2013.01); *C12N 15/1079* (2013.01); *C12N 15/1082* (2013.01); *C12N 15/11* (2013.01); *C12Q 1/68* (2013.01); *C40B 30/06* (2013.01); *C40B 40/08* (2013.01); *C12N 15/81* (2013.01); *C12N 15/905* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| 6,324,479 B1 | 11/2001 | Friend et al. |
| 2005/0079619 A1 | 4/2005 | Roemer et al. |
| 2007/0161031 A1 | 7/2007 | Trinklein et al. |

FOREIGN PATENT DOCUMENTS

| WO | WO-2014204726 A9 * | 12/2014 | ......... A01K 67/0275 |
| WO | 2016/049258 A2 | 3/2016 | |

OTHER PUBLICATIONS

Koszela, J. "Novel Screening Methods for Inhibitors of the Human Ubiquitin-Conjugating Enzymes," Thesis, The University of Edinburgh, Jun. 28, 2014 (Jun. 28, 2014), pp. 1-182 (only pp. 1-103 provided). Retrieved from the Internet: <https://www.era.lib.ed.ac.uk/bitstream/handle/1842/17893/Koszela2014 .pdf? sequence=1 &isAllowed=y> on Sep. 20, 2017 (Sep. 20, 2017). entire document.
Liu et al. "Construction of a Gal1-Regulated Yeast Cdna Expression Library and Its Application to the Identification of Genes Whose Overexpression Causes Lethality in Yeast," Genetics, Nov. 1, 1992 (Nov. 1, 1992), vol. 132, No. 3, pp. 665-673. entire document.
Smith et al. "A Survey of Yeast Genomic Assays for Drug and Target Discovery," Pharmacology & Therapeutics, May 28, 2010 (May 28, 2010), vol. 127, Iss. 2, pp. 156-164. entire document.

* cited by examiner

*Primary Examiner* — Nancy J Leith
*Assistant Examiner* — Jessica D Parisi
(74) *Attorney, Agent, or Firm* — Banner & Witcoff, Ltd.

(57) ABSTRACT

A method of screening is provided including providing a combination of a plurality of proliferating cell types wherein each proliferating cell type has a unique associated barcode within its genome that is different from other proliferating cell types of the plurality and wherein each proliferating cell type includes an exogenous gene that when expressed produces an associated phenotype to the proliferating cell type which alters proliferation of the cell type, introducing a perturbation to one or more of the plurality of proliferating cell types, inducing expression of one or more of the exogenous genes, determining the relative number of unique associated barcodes after a period of proliferation, and comparing the relative number of unique associated barcodes to a control relative number of unique associated barcodes to indicate the effect of the perturbation on the one or more of the plurality of proliferating cell types.

23 Claims, 11 Drawing Sheets
Specification includes a Sequence Listing.

METHODS OF SCREENING USING BARCODED LIBRARIES

RELATED APPLICATIONS

This application is a National Stage Application under 35 U.S.C. 371 of co-pending PCT application PCT/US17/40853 designating the United States and filed Jul. 6, 2017; which claims the benefit of U.S. provisional application No. 62/358,878 filed on Jul. 6, 2016 each of which are hereby incorporated by reference in their entireties.

STATEMENT OF GOVERNMENT INTERESTS

This invention was made with government support under CA009216, HG005550, and HG008525 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jan. 4, 2019, is named "19528020_1.txt" and is 21,487 bytes in size.

BACKGROUND

Methods of screening using model organisms are known. However, existing genetic and small molecule screening methods are costly, labor intensive and non-scalable.

SUMMARY

The present disclosure provides for the use of cell proliferation and differing growth rates between different cell lines or strains to screen for candidate compounds or treatment modalities. If cells under a given set of conditions are exhibiting growth rates below the maximum possible growth rate, for example, because of the presence of a toxic protein associated with a disease state, and a given cell line or variant is able to exhibit a higher growth rate in response to a given permutation, then the cell line or variant will dominate the cell pool over time and the permutation will be identified as a candidate for treatment of the disease associated with the toxic protein.

A proliferating cell type is genetically modified to include an exogenous gene to produce an exogenous protein resulting in an altered cell type. The altered cell type is analyzed to determine a phenotype resulting from the exogenous protein. The proliferating normal or healthy cell type (unaltered cell type) or the altered cell type may also include a nucleic acid barcode unique to the cell type. The nucleic acid barcode may be sequenced and counted to determine the number of cells representing the proliferating cell type or the altered cell type. According to one aspect a plurality of altered cell types may be provided with each altered cell type being genetically modified to include a different exogenous gene to produce an exogenous protein and a nucleic acid barcode unique to each altered cell type. According to one aspect, an altered cell type exhibits a phenotype produced by the exogenous protein. In this manner, the plurality of altered cell types (having associated phenotypes) may be sequenced and the nucleic acid barcodes counted to determine the relative number of cells in each altered cell type.

The exogenous protein is responsible for a phenotype in the cell type, such as reduced growth. The exogenous gene and its associated protein may be linked to a particular disease or condition. Accordingly, the proliferating cell type that is genetically modified to express an exogenous gene to produce an exogenous protein provides a model system to study the exogenous gene and its associated exogenous protein to identify compounds or treatment modalities that reverse or alter the phenotype. According to one aspect, the exogenous protein is toxic to the cell type such that it results in reduced or slowed or inhibited growth of the cell type. In this manner, the exogenous protein is said to be toxic to the cell type. The unaltered or normal cell type exhibits a much faster growth rate compared to the altered cell type where growth or proliferation is impaired. When the unaltered or normal cell type is mixed or placed with the altered cell type, the unaltered cell type overtakes the altered cell type after a proliferation period. However, the altered cell type may be contacted with a candidate compound or otherwise subjected to a permutation event, such as modulation or editing of a target nucleic acid, and the altered cell type growth may be determined. If the candidate compound or other permutation event counters the toxic effect of the exogenous protein, then the altered cell type grows at an increased rate compared to the altered cell type without the candidate compound or other permutation event, thereby identifying a possible treatment for the disease state associated with the exogenous protein. In this manner, a plurality of altered cell types each with its own different exogenous gene and its own unique barcode may be provided in a combination or mixture which may then be subjected to a candidate compound or other permutation event. After a suitable growth period after the permutation, the combination or mixture may be sequenced and the plurality of barcodes counted and the number of cells of each altered cell type determined. In this manner, cell types that have increased in number identify the candidate compound or other permutation event as a possible treatment modality since the toxic effect of the exogenous protein was rescued or altered. Accordingly, a method is provided for screening factors that enable the rescue of growth defects induced by various toxic proteins to identify drugs or genes that influence toxicity of the exogenous protein.

According to the present disclosure, a method of screening is provided that includes providing a combination of a plurality of proliferating cell types wherein each proliferating cell type has a unique associated barcode within its genome that is different from other proliferating cell types of the plurality and wherein each proliferating cell type includes an exogenous gene that when expressed produces an associated phenotype to the proliferating cell type which alters proliferation of the cell type, introducing a perturbation to one or more of the plurality of proliferating cell types, inducing expression of one or more of the exogenous genes, determining the relative number of unique associated barcodes after a period of proliferation, and comparing the relative number of unique associated barcodes to a control relative number of unique associated barcodes to indicate the effect of the perturbation on the one or more of the plurality of proliferating cell types. According to one aspect, wherein expression of the exogenous gene produces an associated phenotype to the proliferating cell type which reduces proliferation of the cell type. According to one aspect, the endogenous gene is a toxicity gene that when expressed causes toxicity to the proliferating cell type thereby reducing proliferation of the proliferating cell type. According to one aspect, the perturbation is a chemical perturbation. According to one aspect, the perturbation is a genetic perturbation. According to one aspect, the control relative number of unique associated barcodes is determined by providing a combination of a plurality of proliferating cell types wherein each proliferating cell type has a unique associated barcode that is different from other proliferating cell types of the plurality and wherein each proliferating cell type has an exogenous gene that when expressed produces an associated phenotype to the proliferating cell type which alters proliferation of the proliferating cell type, inducing expression of one or more of the exogenous genes, and determining the control relative number of unique associated barcodes after a period of proliferation. According to one aspect, the perturbation is accomplished by introduction of a candidate compound to the combination of the plurality of proliferating cell types. According to one aspect, the perturbation is accomplished by introduction of a candidate drug compound to the combination of the plurality of proliferating cell types, wherein the candidate drug compound inhibits the associated phenotype. According to one aspect, the perturbation is accomplished by inducing expression of a target gene within the combination of the plurality of proliferating cell types. According to one aspect, the perturbation is accomplished by reducing expression of a target gene within the combination of the plurality of proliferating cell types. According to one aspect, the relative number of unique associated barcodes is determined by sequencing of the genome of the plurality of proliferating cell types. According to one aspect, the proliferating cell type is yeast or bacteria.

The disclosure provides a method of screening including providing a yeast strain transformed with a plurality of vectors, with each vector in the plurality comprising a first nucleic acid sequence encoding a toxicity gene that when overexpressed causes toxicity to the yeast strain, a guide RNA having a spacer sequence complementary to a target nucleic acid sequence in the genome of the yeast strain, and a unique barcode associated with the toxicity gene and the guide RNA, and introducing an RNA guided DNA binding protein to the yeast strain, inducing expression of the first nucleic acid sequence of the plurality of vectors such that the toxicity gene is expressed and the guide RNA is produced within the yeast strain and colocalizes with the RNA guided DNA binding protein at the target nucleic acid sequence in the genome of the yeast strain and wherein the target nucleic acid is modulated, determining the relative number of unique barcodes associated with the toxicity gene and the guide RNA after a period of proliferation, and comparing the relative number of unique barcodes associated with the toxicity gene and the guide RNA to a control relative number of unique barcodes to indicate the effect of the modulation of the target nucleic acid on the yeast strain. According to one aspect, the RNA guided DNA binding protein is a Cas protein.

Further features and advantages of certain embodiments of the present invention will become more fully apparent in the following description of embodiments and drawings thereof, and from the claims.

DETAILED DESCRIPTION

Figure 1A:
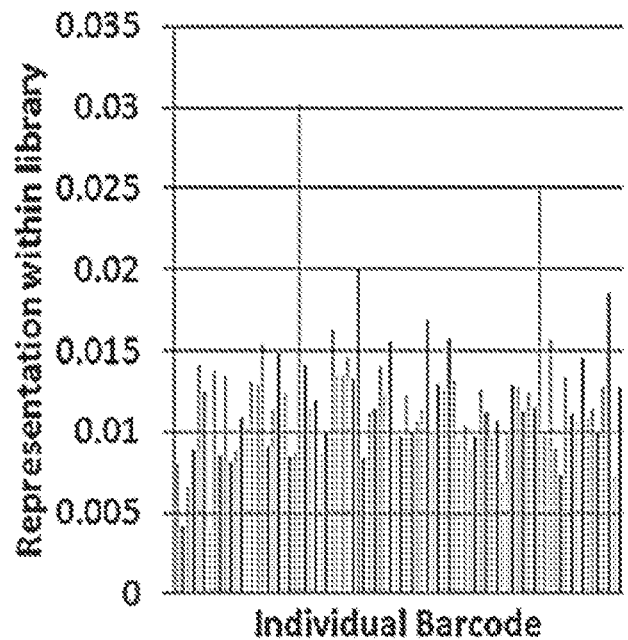
FIG. 1A is a graph depicting barcode number for various yeast strains.

The present disclosure provides screening methods based on alteration of cell growth or proliferation as an indication of modulating the phenotypic effect of an exogenous protein on a cell. For example, when an exogenous protein that causes cellular toxicity is expressed, one phenotype to quantify is a decrease in growth rate. Perturbations, such as chemical or small molecule or genetic editing or regulation, that ameliorate toxicity are discerned by observing a restoration of cell division. Perturbations that enhance toxicity are typified by further reductions in cell growth as compared to control conditions. The exogenous protein can be inhibited or activated, such as by introduction of one or more candidate compounds or by altering one or more genes within the cell, such as gene activation or inhibition. The growth rate (or absolute number of cells) for the cell type is determined. This may be referred to as a normal control cell growth rate. The cell type is altered to include an exogenous protein, such as by providing the cell with an exogenous gene encoding the exogenous protein, thereby producing a genetically altered cell type or strain. The cell expresses the exogenous gene and the phenotypic effect of the exogenous protein of the exogenous gene is determined. In one aspect, cell growth rate is lowered as a result of the exogenous protein. Accordingly, one phenotypic effect of an exogenous protein is a lowering or slowing of cell growth rate compared to the cell type without the exogenous protein. The growth rate of the cell type with the exogenous protein is determined. This may be referred to as an exogenous protein control cell growth rate. The cell type with the exogenous protein is then subjected to a perturbation event. Exemplary perturbation events include introduction of one or more candidate compounds, such as chemicals or small molecules or drug or biologics. Exemplary perturbation events include altering expression of one or more genes within the cell, such as by gene activation or inhibition or gene cutting or gene nicking. The growth rate of the cell type with the exogenous protein and subjected to the perturbation event is determined. This may be referred to as a perturbation event cell growth rate. According to one aspect, the perturbation event cell growth rate is compared to the exogenous protein control cell growth rate and/or the normal control cell growth rate to determine whether the perturbation inhibits the exogenous protein, activates the exogenous protein or has no effect on the exogenous protein, as determined by cell growth rate after a proliferation or growth period. It is to be understood that the number of cells can also be determined and compared for the normal cell type, the cell type including the exogenous protein and the cell type including the exogenous protein and subjected to the perturbation. Whether the perturbation inhibits the exogenous protein, activates the exogenous protein or has no effect on the exogenous protein is based on the increase or decrease in the number of cells after a perturbation period.

The disclosure provides methods of using a combination or mixture of a plurality of proliferating cell types, such as different strains of yeast or bacteria, with each cell type (i.e., each strain of yeast or bacteria) having a particular exogenous protein. The term "cell type" may be used interchangeably with "strain." According to one aspect, the methods employ greater than 5 cell types or strains, greater than 10 cell types or strains, greater than 20 cell types or strains, greater than 30 cell types or strains, greater than 40 cell types or strains, greater than 50 cell types or strains, greater than 60 cell types or strains, greater than 70 cell types or strains, greater than 80 cell types or strains, greater than 90 cell types or strains, greater than 100 cell types or strains, greater than 150 cell types or strains, greater than 200 cell types or strains, greater than 300 cell types or strains, greater than 400 cell types or strains, greater than 500 cell types or strains, greater than 600 cell types or strains, greater than 700 cell types or strains, greater than 800 cell types or strains, greater than 900 cell types or strains, greater than 1000 cell types or strains, greater than 2000 cell types or strains, greater than 3000 cell types or strains, and the like. Each cell type or strain including a particular exogenous protein includes a nucleic acid barcode unique to the cell type or strain. Each cell type or strain including a particular exogenous protein exhibits an altered rate of cell growth or proliferation, i.e. a lowered or slowed rate of cell growth or proliferation, compared to the cell type or strain without the exogenous protein. Determining the number of barcodes within a population of cells, such as by DNA sequencing, is representative of the number of cells in a cell type or strain in the population. In this manner, the number of barcodes is representative of the number of cells in a cell type or strain and an increase or decrease in the number of barcodes is an indication of whether a particular perturbation has inhibited or has activated or has had no effect on the exogenous protein. According to this aspect, a plurality of cell types or strains in a mixture, each having a different exogenous protein and associated growth rate, may be subjected to a particular perturbation and then the growth rates or amount of cells within a cell type or strain may be determined by sequencing the population of cells within the mixture to determine the number of barcodes. The number of barcodes indicates the number of cells of a cell type or strain present after a perturbation period and, therefore, indicates whether the growth rate of a cell type with a particular exogenous protein increased, or decreased or stayed the same in response to the particular perturbation. In this manner, many different cell types or strains with exogenous proteins may be assayed in response to a particular perturbation event.

According to one aspect, the exogenous protein is a toxicity protein, i.e., a protein that has a toxic effect on the cell type into which it is introduced or otherwise contacted. The phenotype of the toxicity protein is a lowered or slowed or declining growth rate in the altered cell type compared to the normal or healthy cell type. The toxicity protein kills the cells or otherwise inhibits proliferation. The cells with the toxic protein have a slower growth rate or lower absolute number of cells (i.e., toxicity control cell growth rate) after a proliferation period compared to the cell type without the toxic protein. The cells including the toxic protein are subjected to a perturbation and cell growth is determined (i.e., perturbation cell growth rate) and compared to the normal control cell growth rate and/or the toxicity control cell growth rate to identify whether the perturbation has decreased toxicity, increased toxicity or has no effect on toxicity, as determined by cell growth rate or absolute number of cells determined after a proliferation period. According to one aspect, the cell type including a particular toxic protein includes a nucleic acid barcode unique to the cell type. Determining the number of barcodes within a population of cells, such as by DNA sequencing, is representative of the number of cells in the population. In this manner, the number of barcodes is representative of the number of cells and an increase or decrease in the number of barcodes is an indication of whether a particular perturbation has decreased or increased toxicity. A plurality of cell types with each cell type having an exogenous protein and a bar code unique to that cell type and different from other cell types may be assayed or screened for whether a particular perturbation rescues the cell type from the toxic effect of the exogenous protein. After the perturbation is introduced to a mixture of the plurality of cell types, the mixture is sequenced after a perturbation period and the number of unique barcodes is counted to determine whether growth of any particular cell type increased as a result of the perturbation, thereby serving as an indication that the perturbation countered the toxic effect of the exogenous protein.

According to one aspect, the disclosure provides a method of screening for an effect of a candidate compound or other permutation event on genetically altered strains of proliferating cells such as yeast strains or bacterial strains. With yeast strains being exemplary, a set of yeast strains are provided with each yeast strain being represented by a unique nucleic acid or DNA barcode. The growth or proliferation rate for a particular or normal yeast strain is determined or known such that the number of cells of a yeast strain after a growth or proliferation period is known or determinable. Each yeast strain is genetically modified to include a particular gene that when expressed or overexpressed produces a protein that may cause toxicity to the yeast strain and thereby may reduce growth or proliferation of the yeast strain compared to the unaltered or normal yeast strain. Exemplary genes are those which are associated with human neurodegenerative diseases such as Alzheimer's disease, Parkinson's disease, amyotrophic lateral sclerosis, frontotemporal dementia, spinocerebellar ataxia and the like. The yeast strains are mixed together in a pool and the yeast strains produce the proteins associated with the particular genes and, after a proliferation or growth period, the relative number of each unique barcode within the pool of cells is analyzed, for example using amplification and sequencing methods known to those of skill in the art. The number of each unique barcode serves as a proxy for the number of cells in each yeast strain. Barcodes associated with toxic proteins will show a decrease in abundance within the population or pool of cells. The pool of altered yeast strains with each having a particular growth rate is contacted with a candidate compound or otherwise subjected to a permutation event and the relative number of each unique barcode within the pool of cells is analyzed, for example using amplification and sequencing methods known to those of skill in the art. Candidate compounds or other permutation events include chemical compounds, small molecules, drugs, biologics, gene overexpression, gene underexpression, gene knockouts, single nucleotide polymorphisms and the like. A candidate compound or other permutation event that rescues or inhibits or prevents or reduces the toxicity of a given protein to a yeast strain will prevent a decrease in the relative representation of the barcoded strain within the pool, i.e. the growth or proliferation of the altered yeast strain will increase in the presence of the candidate compound or other permutation event relative to the growth or proliferation of the altered yeast strain in the absence of the candidate compound or other permutation event at a greater rate. The change in different barcodes are determined or examined for a plurality of candidate compounds or other permutation events to identify candidate compounds or other permutation events that influence or affect toxicity of the protein to the altered yeast strain.

Exemplary Proliferating Cell Types

Proliferating cell types or organisms useful in the methods described herein are those which proliferate at a rate sufficient to carry out experiments in a desirable period of time. The proliferating cell types or organisms are also capable of expressing a phenotype associated with an exogenous protein, such as a toxic protein. According to one aspect, exemplary proliferating cell types are capable of exhibiting a lowering of cell growth in response to the presence of an endogenous protein that is toxic to the cell type. The proliferating cell type or organism may be genetically altered to include the toxicity gene which is expressed by the cell or otherwise induced to be expressed to produce the toxic protein.

Exemplary proliferating cell types include eukaryotic cells or prokaryotic cells.

Exemplary eukaryotic cells include yeast strains or fungus strains.

Exemplary yeast strains include *Saccharomyces cerevisia* (and subtypes such as S288C, CEN.PK etc), genus *Saccharomyces* (e.g., *S. cerevisiae*, *S. bayanus*, *S. boulardii*, *S. pastorianus*, *S. rouxii* and *S. uvarum*), *Schizosaccharomyces* (e.g., *S. pombe*), *Kluveromyces* (e.g., *K. lactis* and *K. fragilis*), genus *Candida* (*C. albicans*, *C. krusei* and *C. tropicalis*) and *Pichia pastoris* and the like.

Exemplary fungus strains include *Aspergillus nidulans, A. oryza, A. niger, A. sojae* and the like.

Exemplary eukaryotic cells include mammalian cells.

Exemplary mammalian cells include HEK 293, Chinese Hamster Ovary cells, HEK 293F, HEK 293H, HEK 293A, HEK 293FT, HEK293T, CHO DG44, CHO-S, CHO-DXB11, Expi293F, ExpiCHO-S, T-Rex, Hela, MCF7, COST, NIH 3T3, U2OS, A375, A549, N2A, PGP1 iPS, BHK, Hap1, Jurkat, N0 and the like.

Exemplary prokaryotic cells include bacteria strains. Exemplary bacterial strains include *E. coli, B. subtilis, S. aureus, S. typhi, M genitalium, V cholera, P. putida* and the like.

Exemplary Exogenous Genes

Exemplary toxicity genes are those responsible for or otherwise involved in a particular disease or disease state. Exemplary toxicity genes include Abeta, Androgen receptor (AR), a-syn A30P, a-syn A53T, a-syn WT, ataxin1, Ataxin1 [Q84], ataxin3, ATXN7, C9orf72 GA100, C9orf72 GA200, C9orf72 GA50, C9orf72 GR100, C9orf72 GR50, C9orf72 PR50, CHOPS M8, CHOPS Wt, EWSR1, EWSR1c1655t, EWSR1g1532c, EWSR1g1750a, FUS WT, FUS-P525L, hnRNPA1 WT, hnRNPA1D262V, hnRNPA2B1 D290V, hnRNPA2B1WT, htt72Q, htt103Q, Htt46Q, PABPN1, SOD1 A4V, SOD1 G85R, SOD1 G93A, SOD1 WT, TAF15, TAF15c1222t, TAF15g1172a, Tau, TDP43, TDP-43 G294A, TDP-43 M337V, TDP-43 Q331K, UBQLN2, CHMP2B, PABPN1, ARX, SOX3, RUNX2, ZIC2, PHOX2B, HOXD13, HOXA13, FOXL2, ATXN2, CACNA1A, PrP, and TBP.

Exemplary Methods of Modifying a Cell Type with an Exogenous Nucleic Acid

Cell types according to the present disclosure may be modified to include one or more exogenous nucleic acids which are expressed by the cell to produce an exogenous protein. As an example, yeast cells may be genetically modified using methods known to those of skill in the art including by LiAc, Electroporation, Biolistic transformation as described in Kawai S, Hashimoto W, Murata K. Transformation of *Saccharomyces cerevisiae* and other fungi: Methods and possible underlying mechanism. Bioengineered Bugs. 2010; 1(6):395-403 hereby incorporated by reference in its entirety.

Amplification Methods

Nucleic acids within cells of a pool of proliferating cells, such as yeast or bacteria or mammalian cells, may be amplified using methods known to those of skill in the art. Exemplary amplification methods include contacting a nucleic acid with one or more primers that specifically hybridize to the nucleic acid under conditions that facilitate hybridization and chain extension. Exemplary methods for amplifying nucleic acids include the polymerase chain reaction (PCR) (see, e.g., Mullis et al. (1986) *Cold Spring Haab. Symp. Quant. Biol.* 51 Pt 1:263 and Cleary et al. (2004) *Nature Methods* 1:241; and U.S. Pat. Nos. 4,683,195 and 4,683,202), anchor PCR, RACE PCR, ligation chain reaction (LCR) (see, e.g., Landegran et al. (1988) *Science* 241:1077-1080; and Nakazawa et al. (1994) *Proc. Natl. Acad. Sci. U.S.A.* 91:360-364), self sustained sequence replication (Guatelli et al. (1990) *Proc. Natl. Acad. Sci. U.S.A.* 87:1874), transcriptional amplification system (Kwoh et al. (1989) *Proc. Natl. Acad. Sci. U.S.A.* 86:1173), Q-Beta Replicase (Lizardi et al. (1988) *BioTechnology* 6:1197), recursive PCR (Jaffe et al. (2000) *J. Biol. Chem.* 275:2619; and Williams et al. (2002) *J. Biol. Chem.* 277:7790), the amplification methods described in U.S. Pat. Nos. 6,391, 544, 6,365,375, 6,294,323, 6,261,797, 6,124,090 and 5,612, 199, isothermal amplification (e.g., rolling circle amplification (RCA), hyperbranched rolling circle amplification (HRCA), strand displacement amplification (SDA), helicase-dependent amplification (HDA), PWGA) or any other nucleic acid amplification method using techniques well known to those of skill in the art.

Sequencing Methods

Nucleic acids within cells of a pool of proliferating cells, such as yeast or bacteria or mammalian cells, may be sequenced using methods known to those of skill in the art such as high throughput disclosed in Mitra (1999) *Nucleic Acids Res.* 27(24):e34; pp. 1-6. Sequencing methods useful in the present disclosure include Shendure et al., Accurate multiplex polony sequencing of an evolved bacterial genome, *Science*, vol. 309, p. 1728-32. 2005; Drmanac et al., Human genome sequencing using unchained base reads on self-assembling DNA nanoarrays, *Science*, vol. 327, p. 78-81. 2009; McKernan et al., Sequence and structural variation in a human genome uncovered by short-read, massively parallel ligation sequencing using two-base encoding, *Genome Res.*, vol. 19, p. 1527-41. 2009; Rodrigue et al., Unlocking short read sequencing for metagenomics, *PLoS One*, vol. 28, e11840. 2010; Rothberg et al., An integrated semiconductor device enabling non-optical genome sequencing, *Nature*, vol. 475, p. 348-352. 2011; Margulies et al., Genome sequencing in microfabricated high-density picolitre reactors, *Nature*, vol. 437, p. 376-380. 2005; Rasko et al. Origins of the *E. coli* strain causing an outbreak of hemolytic-uremic syndrome in Germany, *N. Engl. J. Med.*, Epub. 2011; Huffer et al., Labeled nucleoside triphosphates with reversibly terminating aminoalkoxyl groups, *Nucleos. Nucleot. Nucl.*, vol. 92, p. 879-895. 2010; Seo et al., Four-color DNA sequencing by synthesis on a chip using photocleavable fluorescent nucleotides, *Proc. Natl. Acad. Sci. USA.*, Vol. 102, P. 5926-5931 (2005); Olejnik et al.; Photocleavable biotin derivatives: a versatile approach for the isolation of biomolecules, *Proc. Natl. Acad. Sci. USA.*, vol. 92, p. 7590-7594. 1995; US 2009/0062129 and US 2009/0191553.

Exemplary next generating sequencing methods known to those of skill in the art include Massively parallel signature sequencing (MPSS), Polony sequencing, pyrosequencing (454), Illumina (Solexa) sequencing by synthesis, SOLiD sequencing by ligation, Ion semiconductor sequencing (Ion Torrent sequencing), DNA nanoball sequencing, chain termination sequencing (Sanger sequencing), Heliscope single molecule sequencing, Single molecule real time (SMRT) sequencing (Pacific Biosciences) and nanopore sequencing such as is described at world wide website nanoporetech-.com.

EXAMPLE I

The Number of Cells of Different Yeast Strains May be Identified by Unique Barcodes The present disclosure provides a screening method that uses a plurality of DNA barcoded cell lines, such as uniquely barcoded yeast strains. Each yeast strain contains a unique DNA barcode that allows determination of the number of cells of a particular yeast strain within a pool or larger population or mixture of a plurality of different barcoded yeast strains. All barcodes within the population are sequenced and counted and the relative number of cells of each yeast strain is determined. To determine if there exists a strong correlation between a given strain prevalence within a population and the prevalence of its specific barcode upon sequencing, a series of mixed barcoded populations were generated. Three yeast mixtures were generated each containing 80+ uniquely barcoded strains manually mixed at an equal ratio. To this population, an additional uniquely barcoded strain was added that was delivered at a level equal to the other strains already present within the population, 10 times higher than the other strains already present within the population, or 10 times lower than the other strains already present within the population. DNA was extracted from the population of cells and barcodes were amplified out and sequenced.

Figure 1B:
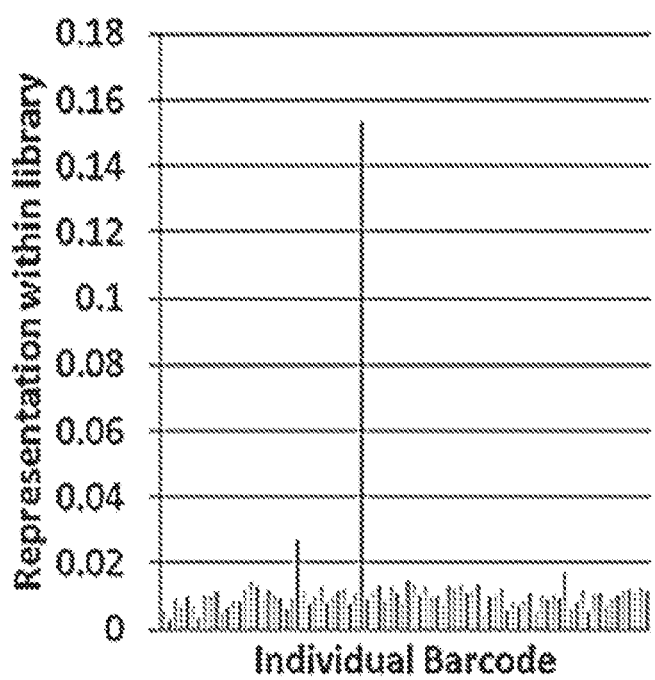
FIG. 1B is a graph depicting barcode number for various yeast strains.
Figure 1C:
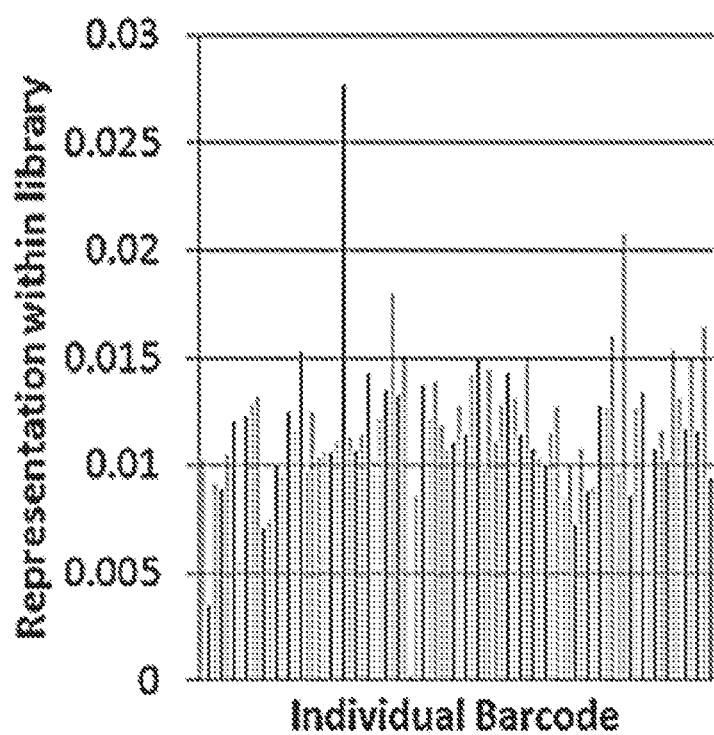
FIG. 1C is a graph depicting barcode number for various yeast strains.

As shown in FIG. 1A, barcode representation correlated well with population structure. In particular, 83 different barcoded yeast strains were mixed together at equal ratios. Into this pool, an additional barcoded strain (noted by red line) was added at a similar ratio. The pool of cells was then lysed and barcodes were amplified from the bulk population and subject to next generation sequencing. In the case where all barcodes (including the additional strain) were mixed at equal ratios, all barcodes within the population were present at a similar ratio to each other. As shown in FIG. 1B, the additional strain (noted by the red line) added at 10 times higher than the other strains already present within the population is shown to be enriched as indicated by its barcode. As shown in FIG. 1C, the additional strain (noted by the red line) added at 10 times lower than the other strains already present within the population is shown to be depleted as indicated by its barcode.

In a second experiment, 40 mixtures were made of 96 different healthy yeast cell strains with each strain having a unique barcode. After one day of growth, the barcodes were amplified and sequenced by a next generation sequencing method. A complex mixture of 94 unique cell lines was able to be detected in a single sample.

EXAMPLE II

Expressing Toxic Proteins Lowers Yeast Cell Growth or Proliferation

The present disclosure provides methods of genetically altering yeast strains to include an exogenous gene encoding a protein toxic to the yeast strain and a barcode associated with the toxic protein and measuring its effect on proliferation.

Aspects of the present disclosure are directed to proteins associated with disease conditions and the use of proliferating cells expressing such proteins as models for screening of candidate compounds or permutation events for their effect on such proteins. According to one aspect, a yeast strain is genetically modified to include a target gene to express a target protein and the altered cells are analyzed to determine whether any particular phenotype of the altered cell is associated with the target protein. In one aspect, the altered strain is analyzed to determine whether the protein has affected the ability of the altered strain to grow or proliferate compared to the unaltered strain. A barcode is used to count the number of cells as a measure of determining whether the protein has affected the ability of the altered strain to grow or proliferate compared to the unaltered strain.

According to one aspect, the target protein is an exogenous protein associated with a neurodegenerative disease. There are several human neurodegenerative diseases that are caused by the accumulation of toxic aggregation prone proteins within neurons. These protein aggregates when present cause cellular dysfunction and ultimately neuronal loss. The toxicity induced by these aggregation prone proteins can be modeled within yeast by overexpressing the given toxic gene and observing its effects on growth rate.

Figure 2A:
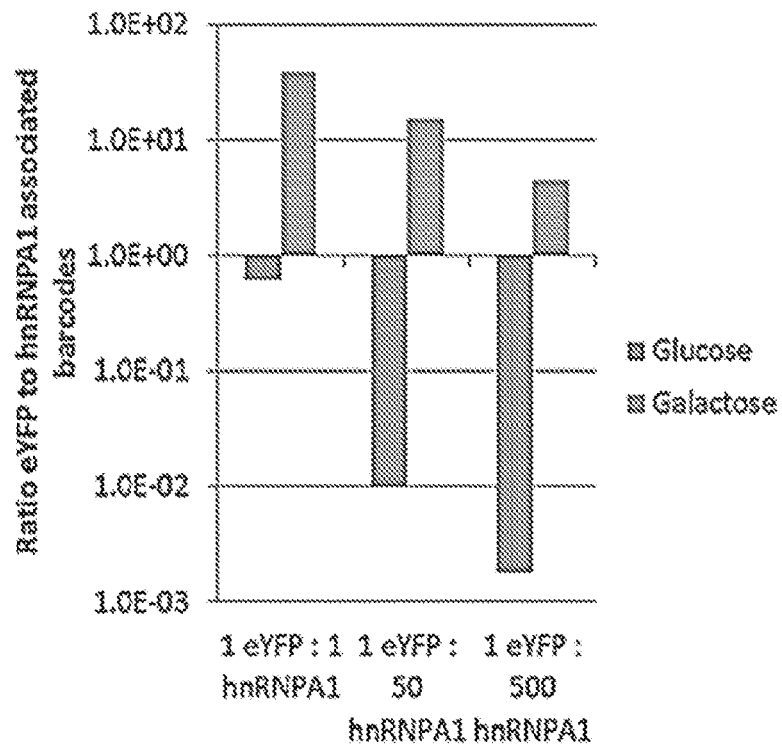
FIG. 2A is a graph demonstrating activation of the hnRNPA1 gene in yeast.
Figure 2B:
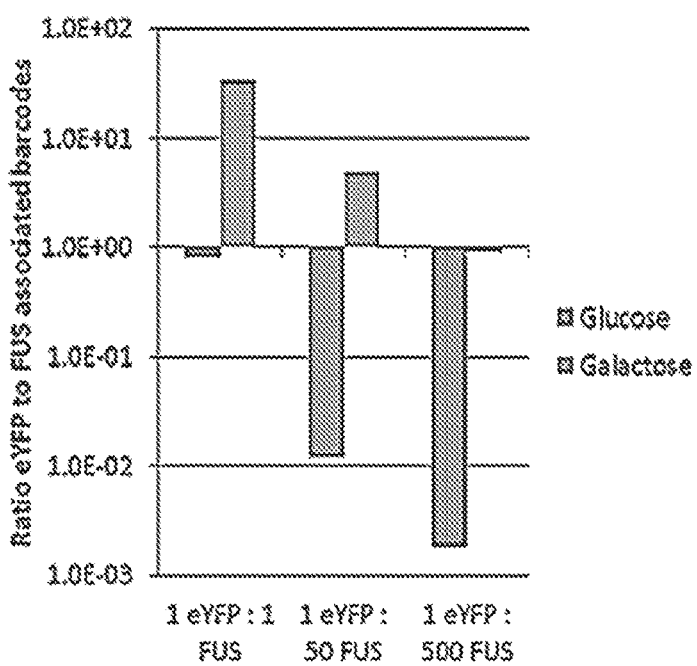
FIG. 2B is a graph demonstrating activation of the FUS gene in yeast.

A multiplexed screening method is provided based on the depletion of barcodes associated with toxic proteins within a pool of altered yeast strains. Three uniquely barcoded yeast strains were genetically modified to include either a control vector that expresses a benign control gene (eYFP) or one of two aggregation prone proteins hnRNPA1 or FUS associated with human neurodegenerative diseases that upon expression causes growth arrest in yeast. (see Kim, H. J. et al. Mutations in prion-like domains in hnRNPA2B1 and hnRNPA1 cause multisystem proteinopathy and ALS. *Nature* 495, 467-473 (2013); Kwiatkowski, T. J. et al. Mutations in the FUS/TLS gene on chromosome 16 cause familial amyotrophic lateral sclerosis. *Science* 323, 1205-1208 (2009) and Vance, C. et al. Mutations in FUS, an RNA processing protein, cause familial amyotrophic lateral sclerosis type 6. *Science* 323, 1208-1211 (2009).) All genes were placed under galactose inducible control and therefore are not expressed when cells are grown in glucose containing media. The genes are induced upon growth in the presence of galactose. The eYFP, hnRNPA1 and FUS containing strains were mixed at 1:1, 1:50 or 1:500 ratios and grown up overnight in either non-inducing (glucose) or inducing (galactose) containing media. The relative ratios of each barcode under non-inducing (glucose) and inducing (galactose) conditions were examined. FIG. 2A depicts results from a mixture of barcoded cells containing either eYFP or hnRNPA1 at various initial seeding ratios under glucose or galactose outgrowth. FIG. 2B depicts results from a mixture of barcoded cells containing either eYFP or FUS at various initial seeding ratios under glucose or galactose outgrowth. As shown in FIGS. 2A and 2B, when placed in non-inducing conditions the relative ratio of each barcode was as expected based on the initial seeding. In contrast, when cells were grown under inducing conditions, despite the eYFP containing strain in some instances being seeded at a 500× lower starting ratio by the end of the outgrowth it was present at nearly an equal ratio or greater to the toxic gene expressing strain. Accordingly, a method is provided for examining barcodes to track growth rates of cells carrying various genetic cargo.

EXAMPLE III

Multiplexing Analysis of a Candidate Compound for its Effect on Toxicity

Figure 3:
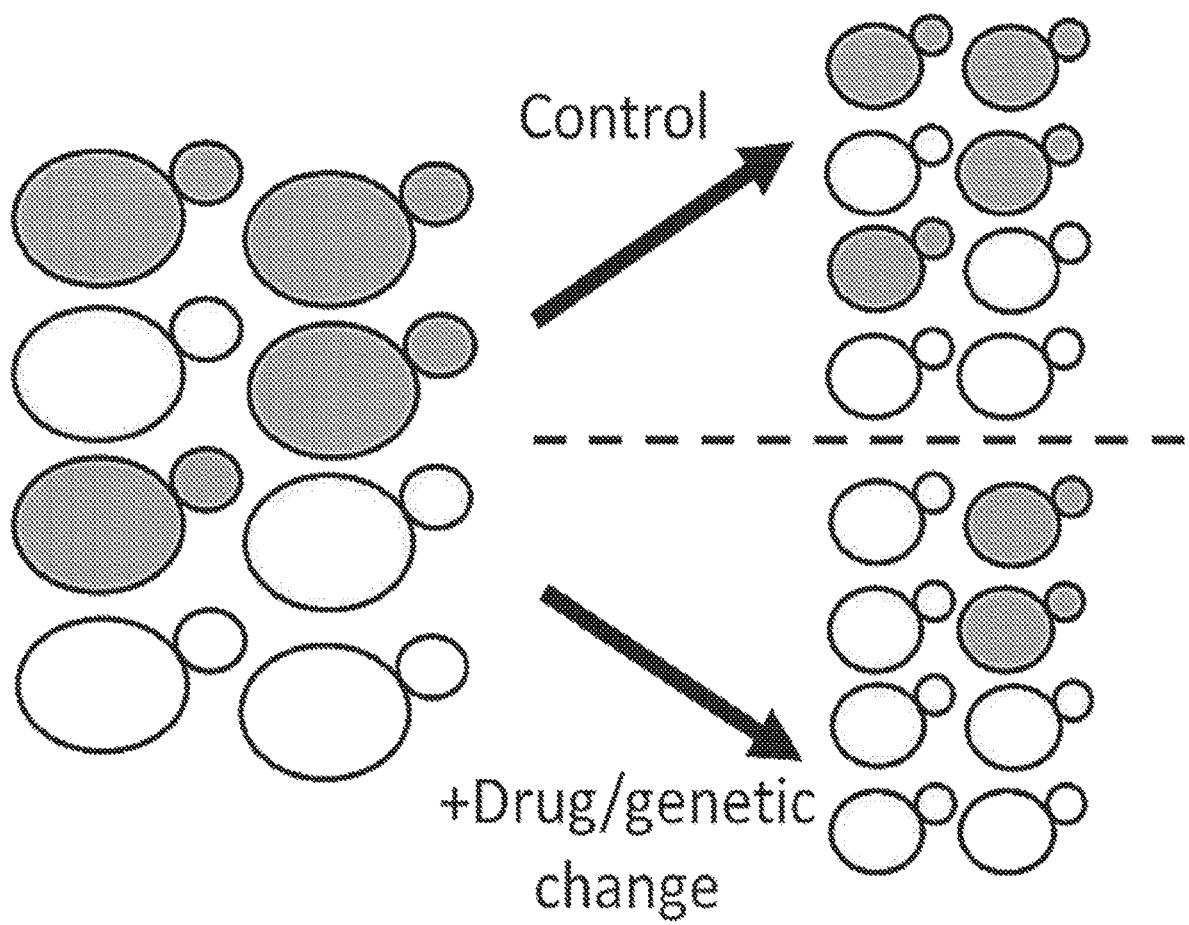
FIG. 3 is an illustration showing rescue of a yeast strain from the toxic effect of an endogenous protein by a drug or a genetic change.

The present disclosure provides methods of screening a candidate compound for its ability to inhibit the toxic effect of a protein on an altered yeast strain within a plurality of altered yeast strains. Depicted in general in FIG. 3, a library of DNA barcoded yeast strains are employed with each uniquely barcoded yeast strain being depicted by a particular color. Each of the barcodes is associated with a different gene of interest some of which cause a growth defect in yeast when expressed. In the control situation, upon expression of the various toxic genes all yeast grow poorly and so no particular strain is enriched upon induction (an equal ratio of each colored yeast strain exists at the beginning as at the end of the screen). When an exogenous drug or a genetic perturbation is introduced into the barcoded yeast strains such that it is able to rescue the slow growth phenotype of one of the strain expressing a toxic gene, the strain enriches over time (depicted by the yellow yeast that enriches over time).

To demonstrate the concept of using DNA barcodes to track growth rate, a library of DNA barcoded yeasts were associated with either control expression plasmids, expression plasmids that carry an aggregation prone protein some of which are associated with neurodegenerative diseases or a gene that causes toxicity in yeast independent of protein aggregation and is not involved in neurodegeneration. Several experiments were conducted in which all members of the library were mixed at equal amounts and the library was grown under non-inducing conditions (glucose) or in the presence of galactose (inducing condition) with or without a small molecule of interest. After overnight outgrowth, genomic DNA was extracted from each of the experimental conditions and barcodes were quantified.

Figure 4A:
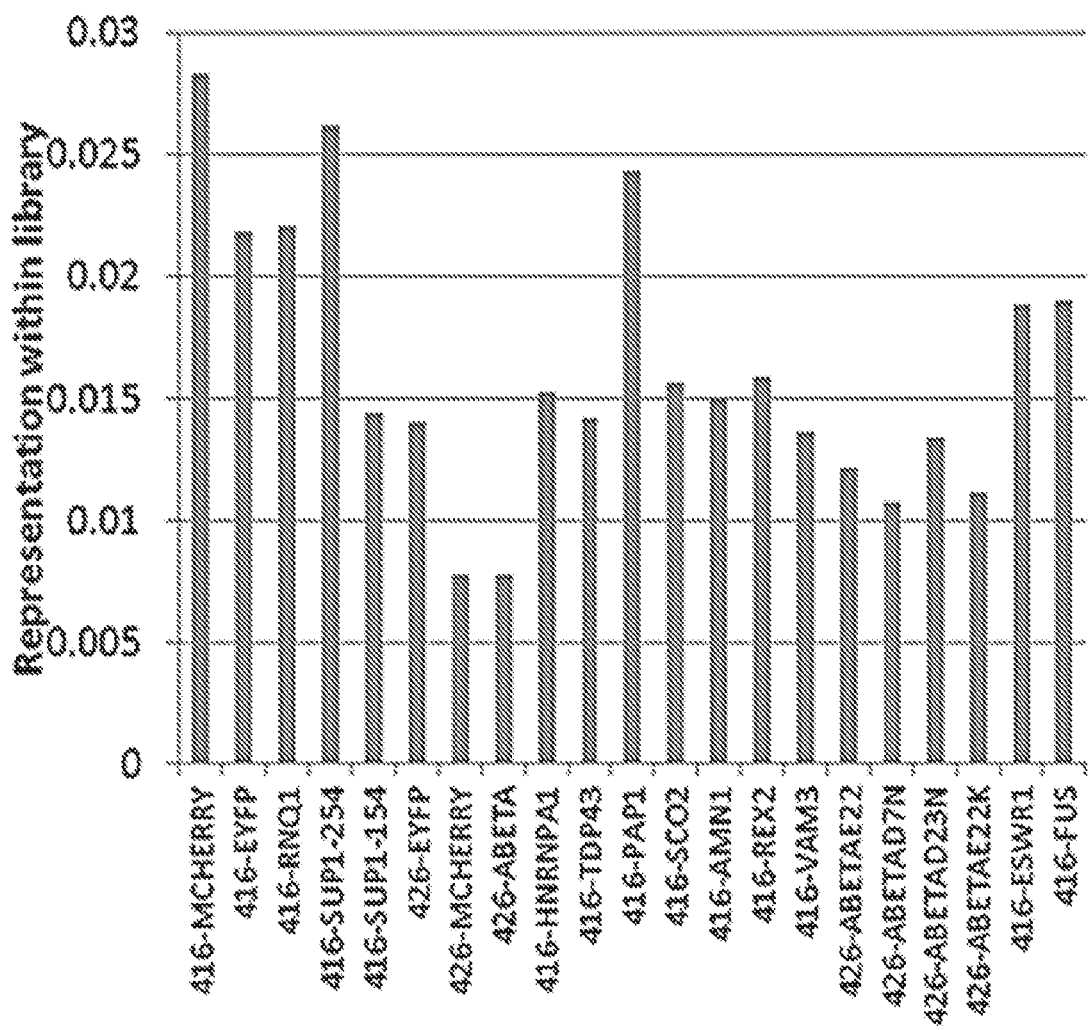
FIG. 4A is a graph showing diversity of barcodes in a series of barcoded yeast strains.
Figure 4B:
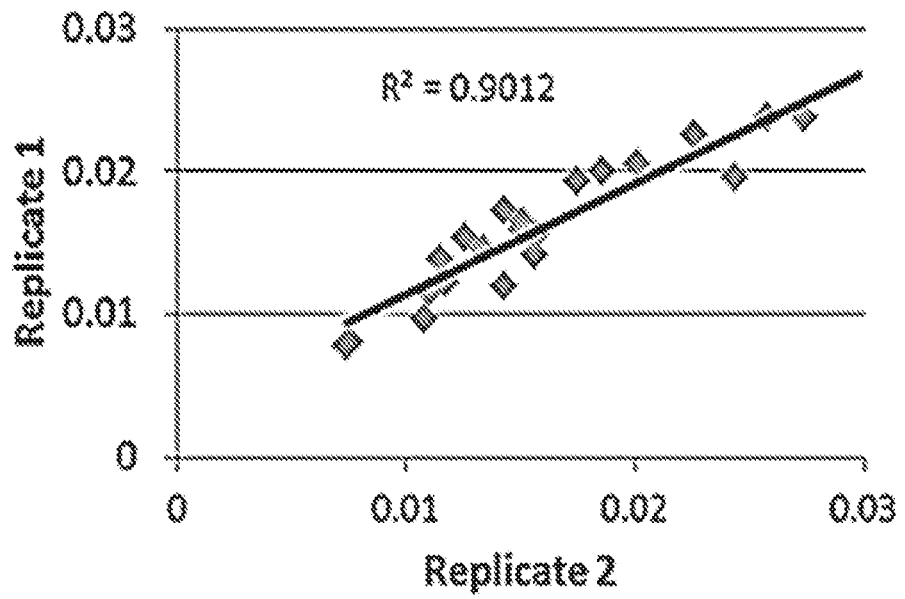
FIG. 4B is a graph showing average representation of the various genes within the library (as determined by barcode sequencing) plotted for two independent biological replicates with the cells being grown under non-inducing conditions.
Figure 4C:
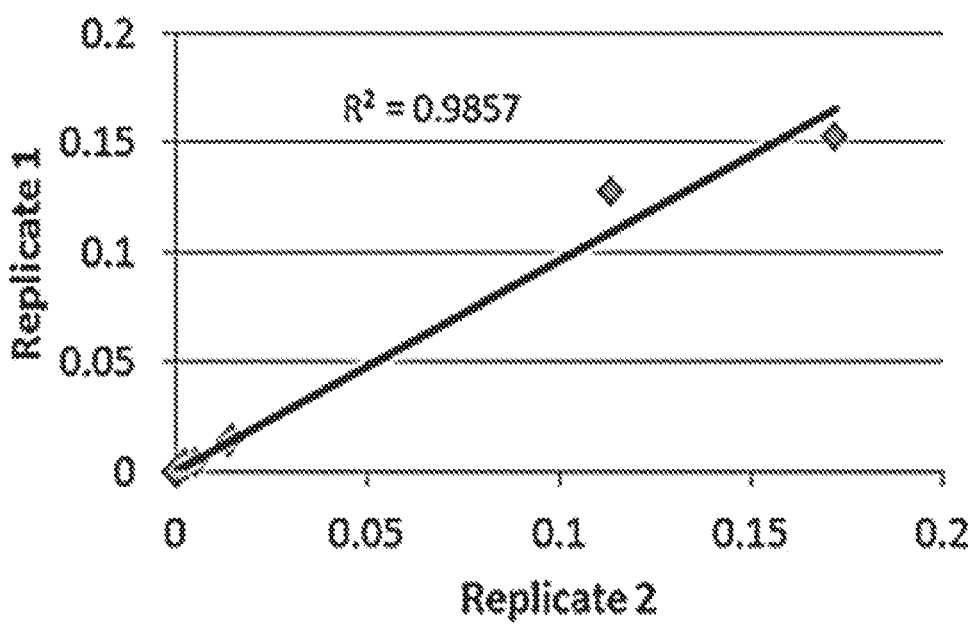
FIG. 4C is a graph showing average representation of the various genes within the library (as determined by barcode sequencing) plotted for two independent biological replicates with the cells being grown under inducing conditions.

With respect to FIG. 4A, a series of barcoded yeast strains each containing a different expression plasmid (denoted on x-axis) were mixed and grown overnight in glucose containing media. The diversity of barcodes within the population was then determined through next-generation sequencing and the average representation for 2-3 replicates of each gene of interest was plotted. Under glucose conditions, the library showed an equal amount of diversity among all of its members with biological replicates showing a high degree of correlation to each other. FIG. 4B depicts the average representation of the various genes within the library (as determined by barcode sequencing) plotted for two independent biological replicates where cells were grown under non-inducing conditions. FIG. 4C depicts the average representation of the various genes within the library (as determined by barcode sequencing) plotted for two independent biological replicates where cells were grown under inducing conditions. "416" and "426" refers to the plasmid background used to express each of the genes tested.

Figure 5A:
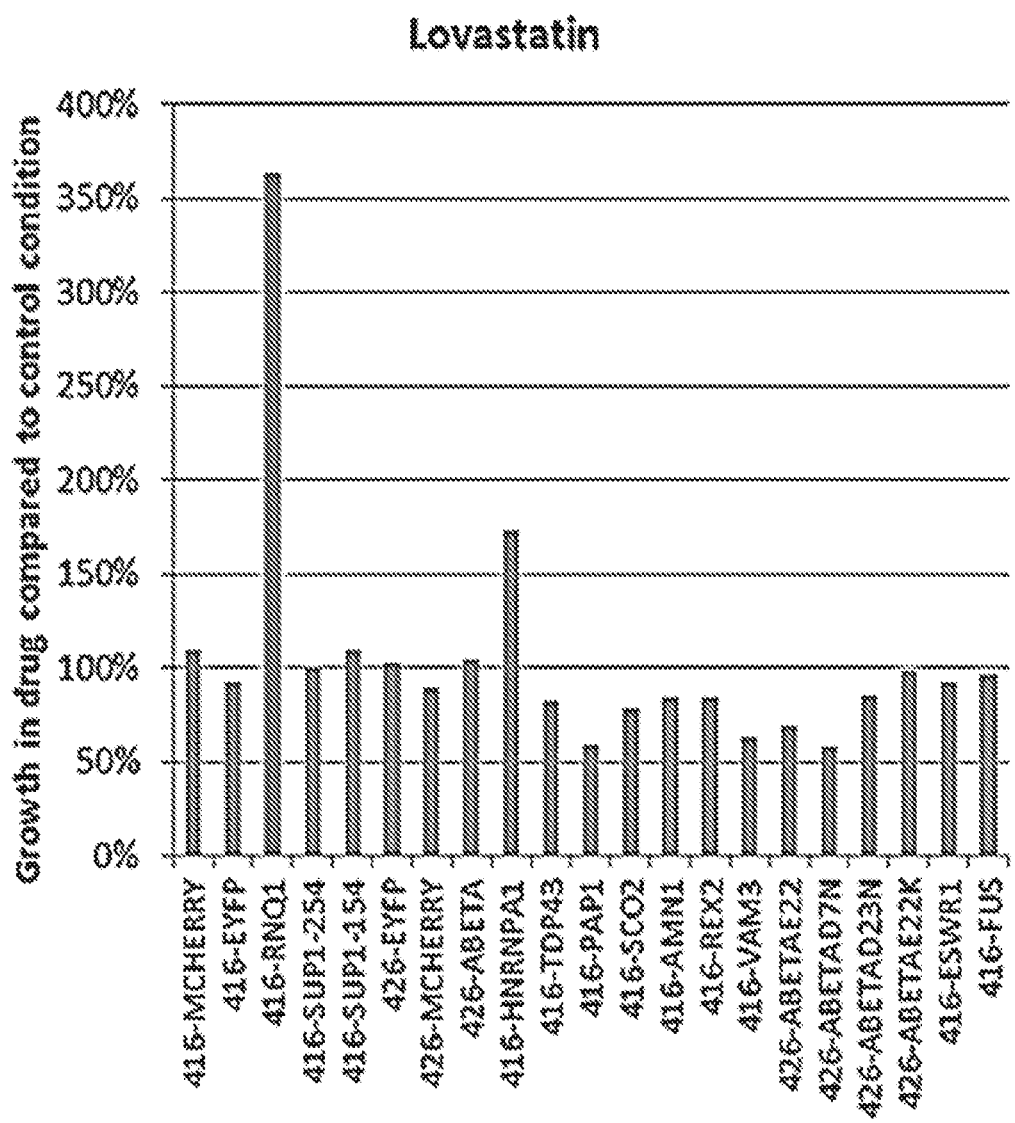
FIG. 5A is a graph showing diversity of barcodes in a series of barcoded yeast in the presence of Lovastatin.
Figure 5B:
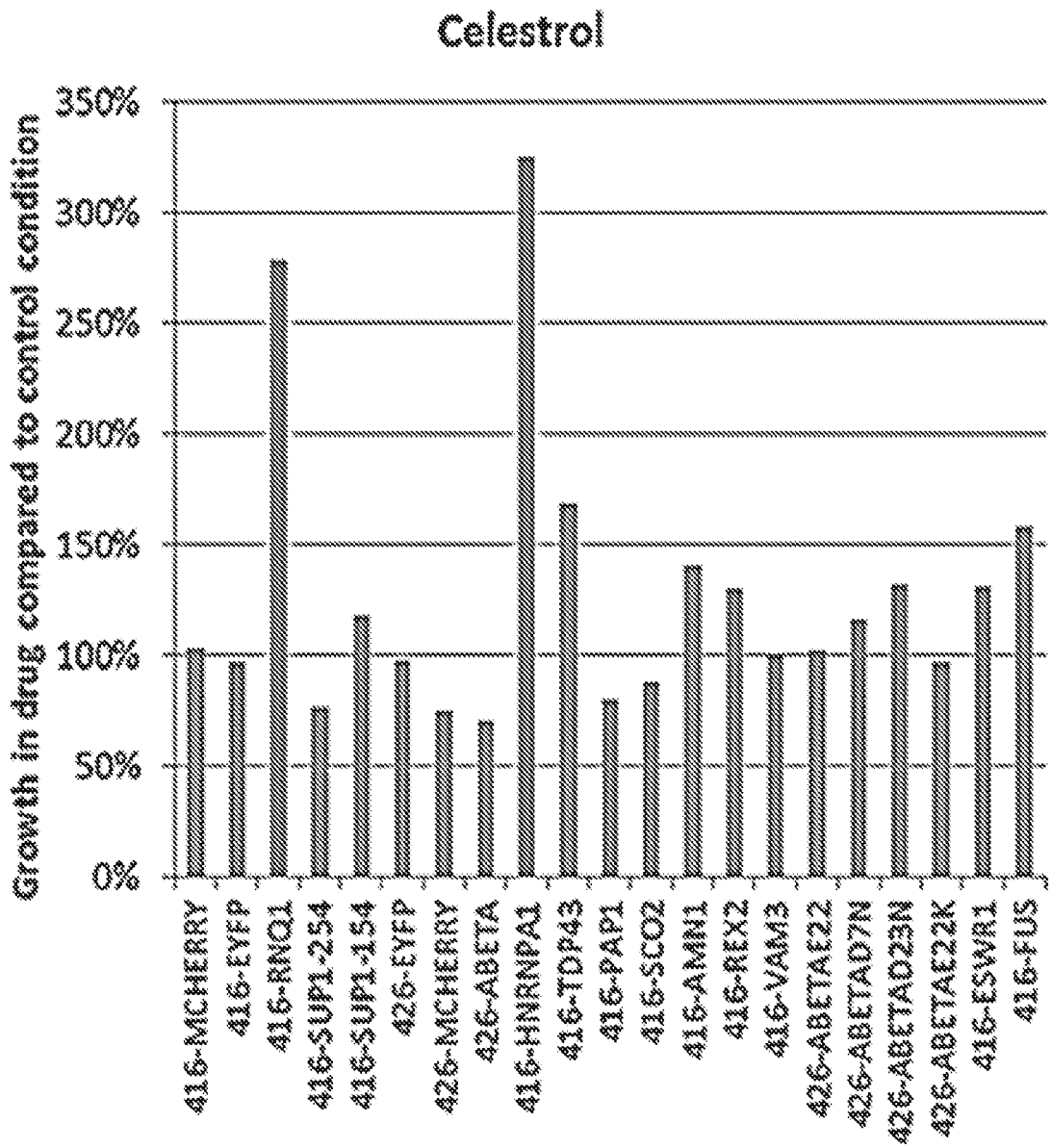
FIG. 5B is a graph showing diversity of barcodes in a series of barcoded yeast in the presence of Celestrol.

A library of barcoded yeast and their associated genes of interest were subjected to growth under inducing conditions in the presence or absence of small molecules. In FIG. 5A, Lovastatin at 2 ug/ml was added to the outgrowth media. In FIG. 5B, Celestrol at 1 ug/ml was added to the outgrowth media. Growth in the presence of drug was normalized to the without drug condition and plotted relative to the no drug condition. Bars highlighted in red represent samples that showed a difference >3 standard deviations as compared to the control no drug condition. "416" and "426" refers to the plasmid background used to express each of the genes tested.

Figure 8:
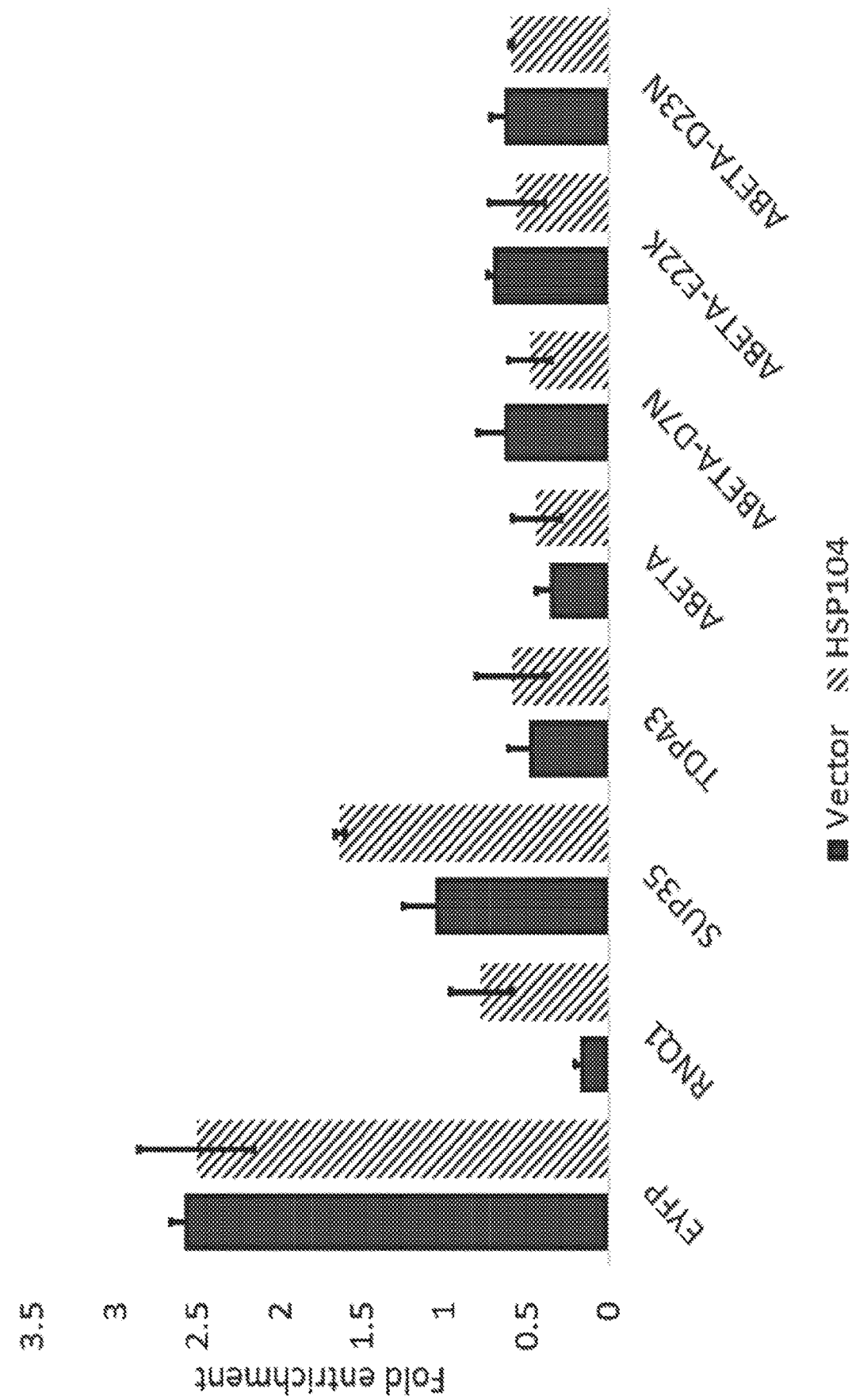
FIG. 8 is a graph of data directed to results of a library experiment using barcode sequencing to quantify the abundance of each member before and after overnight growth in inducing conditions. In addition, library members were grown either in the presence of an empty vector or vector expressing the molecular chaperone HSP104. Error bars ±1 s.d., n=3, *p<0.01.

Both Lovastatin and Celestrol showed an ability to rescue the growth of some of the toxic aggregation prone proteins that were examined. For both Lovastatin and Celestrol at the concentrations that were tested, none of the proteins that cause toxicity in yeast through alternative methods outside of protein aggregation showed significant rescue nor did control strains expressing benign proteins such as eYFP and mCherry exhibit a significant change in their growth, demonstrating that the rescue associated with Lovastatin and Celestrol is specific. According to one aspect, barcoding methods as described herein are used to interrogate the effects of various genetic perturbations on the library en masse. For example, overexpression of HSP104 is able to rescue particular mutants within the population (See FIG. 8).

EXAMPLE IV

Materials and Methods

The present disclosure utilizes the following material and methods in one or more of the Examples described herein.

Yeast Strains and Plasmids

The BY4741/4742 strain background was employed for all experiments. Gateway-compatible pAG CEN/ARS (416) or 2 um (426) destination vectors with galactose inducible promoters were utilized for over-expression experiments. See Alberti, S., Gitler, A. D. & Lindquist, S. A suite of Gateway® cloning vectors for high-throughput genetic analysis in *Saccharomyces cerevisiae*. Yeast 24, 913-919 (2007). Yeast were transformed using the LiAc method as previously described. See Gietz, R. D. & Schiestl, R. H. High-efficiency yeast transformation using the LiAc/SS carrier DNA/PEG method. *Nat. Protocols* 2, 31-34 (2007). All strains were grown at 30° C. in YDP or minimal media with appropriate auxotrophic supplementation. The library of DNA barcoded yeast strains described herein have been previously described. See Ho, C. H. et al. A molecular barcoded yeast ORF library enables mode-of-action analysis of bioactive compounds. *Nat. Biotechnol.* 27, 369-377 (2009).

Barcoded Mixed Pool Experiment

For growth competition experiments, yeast strains each with a unique DNA barcode along with containing a plasmid encoding a control or toxic protein of interest were first grown overnight to saturation in SC-URA+glucose. The various barcoded lines were then mixed in defined ratios and passaged at a 1:1000 dilution into fresh SC-URA+glucose or SC-URA+galactose media. For experiments involving small molecules, yeast were diluted into SC-URA+galactose media containing a given small molecule of interest and allowed to grow for 36 hours before genomic DNA was extracted from the population of cells.

Yeast Lysis

Yeast lysis was performed as previously described. See Lõoke, M., Kristjuhan, K. & Kristjuhan, A. Extraction of genomic DNA from yeasts for PCR-based applications. *BioTechniques* 50, 325-328 (2011). Briefly, 300-900 ul of overnight culture was spun down and resuspended in 300 ul of 200 mM LiAc, 1% SDS solution. Cells were then vortexed several times and incubated at 70° C. for 10-15 minutes. 900 ul of >95% ethanol was then added to the samples and they were inverted several times along with vortexing to mix the solution well. The samples were then spun at 15,000 g for 3 minutes and the supernatant was discarded. Pellets were washed 1× with 70% ethanol, spun at 15,000 g for 3 minutes and the supernatant was again removed. The pellet was then allowed to air dry for 5-10 minutes before adding in 100 ul of 10 mM Tris pH 8.5 and pipetting up and down to break up the pellet. Samples were then placed in a heating block set to 37° C. for 10 minutes, spun again at 15,000 g for 3 minutes and then the supernatant was collected and used in downstream DNA analysis.

Barcode Quantification Using Next Generation Sequencing

Genomic DNA was extracted and barcoded using one of four internally barcoded forward primers, CTTTCCCTA-CACGACGCTCTTCCGATCT NNNN CACAG tttaaactaatatacacattttacgg; CTTTCCCTA-CACGACGCTCTTCCGATCT NNNN GTGTT tttaaactaatatacacattttacgg; CTTTCCCTA-CACGACGCTCTTCCGATCT NNNN TCTTG tttaaactaatatacacattttacgg; CTTTCCCTA-CACGACGCTCTTCCGATCT NNNN AGCTC tttaaactaatatacacattttacgg; in combination with the reverse primer, GGAGTTCAGACGTGTGCTCTTCC-GATCTaacgccgccatccagtttaaacgag. Following PCR, the amplicons were purified and normalized using SequalPrep Normalization Plate (96) kit (Thermo Fisher). A second round of PCR was next performed using the Illumina Truseq adapters in order to allow individual samples to be identified during subsequent data analysis. The reads were aligned to a list of the 96 possible barcodes (see Ho, C. H. et al. A molecular barcoded yeast ORF library enables mode-of-action analysis of bioactive compounds. *Nat. Biotechnol.* 27, 369-377 (2009) using BWA. The depth of coverage for each barcode was calculated for each of the samples using a custom script and normalized to the total number of reads per sample.

Plasmid Synthesis

A landing platform allowing insertion of a disease causing gene was made by digesting pRS413-gal1:TAP-NAT with SpeI/MluI in buffer 2.1 and purifying the backbone from gel. gBlock PAC8404 containing 50 bp overhangs with the plasmid was inserted into the backbone using Gibson assembly (Cat E5510S, New England Biolabs), following manufacturer's instructions to generate pC01. The alpha-synuclein (Genbank NM_000345.3) with a G157A mutation was amplified from plasmid provided by A. Gilter, Stanford University using fw: AAAAACCCCGGAT-TCTAGAAAAATGGATGTATTCATGAAAGGACTT, AAGAAATTCGCATCGAT-TTTTCGCACCAGTTCGGCACATGACCATTATT-AGGCTT CAGGTTCGTAGTCTTGA. The PCR product was inserted into plasmid pC01 (linearized using SpeI/MluI) using Gibson assembly (Cat E5510S, New England Biolabs), following manufacturer's instructions to generate pC08.

Yeast Transformation and Plasmid Detection

BY4741 cells were transformed with the pC08 plasmid and gDNA was purified. The barcode segment was amplified using fw: TGGTCATGTGCCGAACTGG and rv: CGAAACTTCTCCGCAGTGAAAG. The unpurified PCR product was sent for sequencing using primer TGGT-CATGTGCCGAACTGG (Genewiz).

```
Supplemental Sequences:

gBlock PAC8404 containing the landing platform:
CCTCTATACTTTAACGTCAAGGAGAAAAAACCCCGGATTCTAGAACTAGT
GTAGGATCGATGCGAATTTCTTATGATTTATGATTTTTATTATTAAATAA
GTTATAAAAAAAATAAGTGTATACAAATTTTAAAGTGACTCTTAGGTTTT
AAAACGAAAATTCTTAAGACATAAAAAACAAAAAAAGCACCACCGACTCG
GTGCCACTTTTTCAAGTTGATAACGGACTAGCCTTATTTTAACTTGCTAT
TTCTAGCTCTAAAACCGAGACGCATTAATCGTCTCGGATCATTTATCTTT
CACTGCGGAGAAGTTTCGAACGCCGAAACATGCGCACCAACTTTCACTTC
TACAGCGTTTGACCAAAATCTTTTGAACATAACATTGTAGGGTGTGAAAA
AATGCGCACCTTTACCGCTAGCCCAAGAGGGCACTACAAAATCTAGAGTT
GTACTTCAAACGTACATGTAATCCCTTGTATATACTCGAAAGAAAACATC
AAGTTTCTGTATAAATATGAGTGAAAGCATAATCATACATTATCTTTTCA
AAGACGCGTGTACGCATGTAACATTATACTGAAAACCTTGCTTGAGAAGG
TTTTGG Alpha-synuclein (Genbank NM_000345.3) G157A
(mutation marked in BOLD and Italics)
ATGGATGTATTCATGAAAGGACTTTCAAAGGCCAAGGAGGGAGTTGTGGC
TGCTGCTGAGAAAACCAAACAGGGTGTGGCAGAAGCAGCAGGAAAGACAA
AAGAGGGTGTTCTCTATGTAGGCTCCAAAACCAAGGAGGGAGTGGTGCAT
GGTGTGACAACAGTGGCTGAGAAGACCAAAGAGCAAGTGACAAATGTTGG
AGGAGCAGTGGTGACGGGTGTGACAGCAGTAGCCCAGAAGACAGTGGAGG
GAGCAGGGAGCATTGCAGCAGCCACTGGCTTTGTCAAAAAGGACCAGTTG
GGCAAGAATGAAGAAGGAGCCCCACAGGAAGGAATTCTGGAAGATATGCC
TGTGGATCCTGACAATGAGGCTTATGAAATGCCTTCTGAGGAAGGGTATC
AAGACTACGAACCTGAAGCCTAATAA pC01-gal1:alpha-synuclein:barcode:ADHterminator:
guideRNA_expression_cassette
GACGCTCGAAGGCTTTAATTTGCGGCCGGTACCCAATTCGCCCTATAGTG
AGTCGTATTACGCGCGCTCACTGGCCGTCGTTTTACAACGTCGTGACTGG
GAAAACCCTGGCGTTACCCAACTTAATCGCCTTGCAGCACATCCCCCTTT
CGCCAGCTGGCGTAATAGCGAAGAGGCCCGCACCGATCGCCCTTCCCAAC
AGTTGCGCAGCCTGAATGGCGAATGGCGCGACGCGCCCTGTAGCGGCGCA
TTAAGCGCGGCGGGTGTGGTGGTTACGCGCAGCGTGACCGCTACACTTGC
CAGCGCCCTAGCGCCCGCTCCTTTCGCTTTCTTCCCTTCCTTTCTCGCCA
CGTTCGCCGGCTTTCCCCGTCAAGCTCTAAATCGGGGGCTCCCTTTAGGG
TTCCGATTTAGTGCTTTACGGCACCTCGACCCCAAAAAACTTGATTAGGG
TGATGGTTCACGTAGTGGGCCATCGCCCTGATGACGGTTTTTCGCCCTT
TGACGTTGGAGTCCACGTTCTTTAATAGTGGACTCTTGTTCCAAACTGGA
ACAACACTCAACCCTATCTCGGTCTATTCTTTTGATTTATAAGGGATTTT
```

Supplemental Sequences:

```
GCCGATTTCGGCCTATTGGTTAAAAAATGAGCTGATTTAACAAAAATTTA
ACGCGAATTTTAACAAAATATTAACGTTTACAATTTCCTGATGCGGTATT
TTCTCCTTACGCATCTGTGCGGTATTTCACACCGCATAGATCCGTCGAGT
TCAAGAGAAAAAAAAGAAAAAGCAAAAAGAAAAAAGGAAAGCGCGCCTC
GTTCAGAATGACACGTATAGAATGATGCATTACCTTGTCATCTTCAGTAT
CATACTGTTCGTATACATACTTACTGACATTCATAGGTATACATATATAC
ACATGTATATATATCGTATGCTGCAGCTTTAAATAATCGGTGTCACTACA
TAAGAACACCTTTGGTGGAGGGAACATCGTTGGTACCATTGGGCGAGGTG
GCTTCTCTTATGGCAACCGCAAGAGCCTTGAACGCACTCTCACTACGGTG
ATGATCATTCTTGCCTCGCAGACAATCAACGTGGAGGGTAATTCTGCTAG
CCTCTGCAAAGCTTTCAAGAAAATGCGGGATCATCTCGCAAGAGAGATCT
CCTACTTTCTCCCTTTGCAAACCAAGTTCGACAACTGCGTACGGCCTGTT
CGAAAGATCTACCACCGCTCTGGAAAGTGCCTCATCCAAAGGCGCAAATC
CTGATCCAAACCTTTTTACTCCACGCGCCAGTAGGGCCTCTTTAAAAGCT
TGACCGAGAGCAATCCCGCAGTCTTCAGTGGTGTGATGGTCGTCTATGTG
TAAGTCACCAATGCACTCAACGATTAGCGACCAGCCGGAATGCTTGGCCA
GAGCATGCTATCATATGGTCCAGAAACCCTATACCTGTGTGGACGTTAATC
ACTTGCGATTGTGTGGCCTGTTCTGCTACTGCTTCTGCCTCTTTTTCTGG
GAAGATCGAGTGCTCTATCGCTAGGGGACCACCCTTTAAAGAGATCGCAA
TCTGAATCTTGGTTTCATTTGTAATACGCTTTACTAGGGCTTTCTGCTCT
GTCATCTTTGCCTTCGTTTATCTTGCCTGCTCATTTTTTAGTATATTCTT
CGAAGAAATCACATTACTTTATATAATGTATAATTCATTATGTGATAATG
CCAATCGCTAAGAAAAAAAAGAGTCATCCGCTAGGGGAAAAAAAAAAAT
GAAAATCATTACCGAGGCATAAAAAAATATAGAGTGTACTAGAGGAGGCC
AAGAGTAATAGAAAAGAAAATTGCGGGAAAGGACTGTGTTATGACTTCC
CTGACTAATGCCGTGTTCAAACGATACCTGGCAGTGACTCCTAGCGCTCA
CCAAGCTCTTAAAACGGGAATTTATGGTGCACTCTCAGTACAATCTGCTC
TGATGCCGCATAGTTAAGCCAGCCCCGACACCCGCCAACACGCGCTGACG
CGCCCTGACGGGCTTGTCTGCTCCCGGCATCCGCTTACAGACAAGCTGTG
ACCGTCTCCGGGAGCTGCATGTGTCAGAGGTTTTCACCGTCATCACCGAA
ACGCGCGAGACGAAAGGGCCTCGTGATACGCCTATTTTTATAGGTTAATG
TCATGATAATAATGGTTTCTTAGGACGGATCGCTTGCCTGTAACTTACAC
GCGCCTCGTATCTTTTAATGATGGAATAATTTGGGAATTTACTCTGTGTT
TATTTATTYTTATGTTTGTATTTGGATTTTAGAAAGTAAATAAAGGAGG
TAGAAGAGTTACGGAATGAAGAAAAAAAATAAACAAAGGTTTAAAAAAT
TTCAACAAAAAGCGTACTTTACATATATATTTATTAGACAAGAAAAGAG
ATTAAATAGATATACATTCGATTAACGATAAGTAAAATGTAAAATCACAG
GATTTTCGTGTGTGGTCTTCTACACAGACAAGATGAAACAATTCGGCATT
AATACCTGAGAGCAGGAAGAGCAAGATAAAAGGTAGTATTTGTTGGCGAT
CCCCCTAGAGTCTTTTACATCTTCGGAAAACAAAAACTATTTTTCTTTA
ATTTCTTTTTTACTTTCTATTTTAATTTATATATTTATATTAAAAAT
TTAAATTATAATTATTTTTATAGCACGTGATGAAAAGGACCCAGGTGGCA
CTTTTCGGGGAAATGTGCGCGGAACCCCTATTTGTTTATTTTTCTAAATA
CATTCAAATATGTATCCGCTCATGAGACAATAACCCTGATAAATGCTTCA
ATAATATTGAAAAGGAAGAGTATGAGTATTCAACATTTCCGTGTCGCCC
TTATTCCCTTTTTTGCGCATTTTGCCTTCCTGTTTTTGCTCACCCAGAA
ACGCTGGTGAAAGTAAAAGATGCTGAAGATCAGTTGGGTGCACGAGTGGG
TTACATCGAACTGGATCTCAACAGCGGTAAGATCCTTGAGAGTTTTCGCC
CCGAAGAACGTTTTCCAATGATGAGCACTTTTAAAGTTCTGCTATGTGGC
GCGGTATTATCCCGTATTGACGCCGGGCAAGAGCAACTCGGTCGCCGCAT
ACACTATTCTCAGAATGACTTGGTTGAGTACTCACCAGTCACAGAAAAGC
ATCTTACGGATGGCATGACAGTAAGAGAATTATGCAGTGCTGCCATAACC
ATGAGTGATAACACTGCGGCCAACTTACTTCTGACAACGATCGGAGGACC
GAAGGAGCTAACCGCTTYTTTGCACAACATGGGGGATCATGTAACTCGCC
TTGATCGTTGGGAACCGGAGCTGAATGAAGCCATACCAAACGACGAGCGT
GACACCACGATGCCTGTAGCAATGGCAACAACGTTGCGCAAACTATTAAC
TGGCGAACTACTTACTCTAGCTTCCCGGCAACAATTAATAGACTGGATGG
AGGCGGATAAAGTTGCAGGACCACTTCTGCGCTCGGCCCTTCCGGCTGGC
TGGTTTATTGCTGATAAATCTGGAGCCGGTGAGCGTGGGTCTCGCGGTAT
CATTGCAGCACTGGGGCCAGATGGTAAGCCCTCCCGTATCGTAGTTATCT
ACACGACGGGGAGTCAGGCAACTATGGATGAACGAAATAGACAGATCGCT
GAGATAGGTGCCTCACTGATTAAGCATTGGTAACTGTCAGACCAAGTTTA
CTCATATATACTTTAGATTGATTTAAAACTTCATTTTTAATTTAAAAGGA
TCTAGGTGAAGATCCTTTTTGATAATCTCATGACCAAAATCCCTTAACGT
GAGTTTTCGTTCCACTGAGCGTCAGACCCCGTAGAAAAGATCAAAGGATC
TTCTTGAGATCCTTTTTTTCTGCGCGTAATCTGCTGCTTGCAAACAAAAA
AACCACCGCTACCAGCGGTGGTTTGTTTGCCGGATCAAGAGCTACCAACT
CTTTTTCCGAAGGTAACTGGCTTCAGCAGAGCGCAGATACCAAATACTGT
CCTTCTAGTGTAGCCGTAGTTAGGCCACCACTTCAAGAACTCTGTAGCAC
CGCCTACATACCTCGCTCTGCTAATCCTGTTACCAGTGGCTGCTGCCAGT
GGCGATAAGTCGTGTCTTACCGGGTTGGACTCAAGACGATAGTTACCGGA
TAAGGCGCAGCGGTCGGGCTGAACGGGGGGTTCGTGCACACAGCCCAGCT
TGGAGCGAACGACCTACACCGAACTGAGATACCTACAGCGTGAGCTATGA
GAAAGCGCCACGCTTCCCGAAGGGAGAAAGGCGGACAGGTATCCGGTAAG
CGGCAGGGTCGGAACAGGAGAGCGCACGAGGGAGCTTCCAGGGGGAAACG
CCTGGTATCTTTATAGTCCTGTCGGGTTTCGCCACCTCTGACTTGAGCGT
CGATTTTGTGATGCTCGTCAGGGGGGCGGAGCCTATGGAAAAACGCCAG
CAACGCGGCCTTTTTACGGTTCCTGGCCTTTTGCTGGCCTTTTGCTCACA
TGTTCTTTCCTGCGTTATCCCCTGATTCTGTGGATAACCGTATTACCGCC
TTTGAGTGAGCTGATACCGCTCGCCGCAGCCGAACGACCGAGCGCAGCGA
GTCAGTGAGCGAGGAAGCGGAAGAGCGCCCAATACGCAAACCGCCTCTCC
CCGCGCGTTGGCCGATTCATTAATGCAGCTGGCACGACAGGTTTCCCGAC
TGGAAAGCGGGCAGTGAGCGCAACGCAATTAATGTGAGTTACCTCACTCA
TTAGGCACCCCAGGCTTTACACTTTATGCTTCCGGCTCCTATGTTGTGTG
GAATTGTGAGCGGATAACAATTTCACACAGGAAACAGCTATGACCATGAT
TACGCCAAGCGCGCAATTAACCCTCACTAAAGGGAACAAAAGCTGGAGCT
CTAGTACGGATTAGAAGCCGCCGAGCGGGCGACAGCCCTCCGACGGAAGA
CTCCTCCTGCGTCCTCGTCTTCACCGGTCGCGTTCCTGAAACGCAGA
TGTGCCTCGCGCCGCACTGCTCCGAACAATAAAGATTCTACAATACTAGC
TTTTATGGTTATGAAGAGGAAAATTGGCAGTAACCTGGCCCCACAAACC
TTCAAATTAACGAATCAAATTAACAACCATAGGATGATAATGCGATTAGT
TTTTTAGCCTTATTTCTGGGGTAATTAATCAGCGAAGCGATGATTTTTGA
TCTATTAACAGATATATAAATGGAAAAGCTGCATAACCACTTTAACTAAT
ACTTTCAACATTTTCAGTTTGTATTACTTCTTATTCAAATGTCATAAAAG
TATCAACAAAAAATTGTTAATATACCTCTATACTTTAACGTCAAGGAGAA
AAAACCCCGGATTCTAGAACTAGTGTAGGATCGATGCGAATTTCTTATGA
TTTATGATTTTTTATTATTAAATAAGTTATAAAAAAAATAAGTGTATACA
ATTTTAAAGTGACTCTTAGGTTTTAAAACGAAAATTCTTAAGCACATAAA
AACAAAAAAAGCACCACCGACTCGGTGCCACTTTTTCAAGTTGATAACGG
ACTAGCCTTATTTTAACTTGCTATTTCTAGCTCTAAAACCGAGACGCATT
AATCGTCTCGGATCATTTATCTTTCACTGCGGAGAAGTTTCGAACGCCGA
AACATGCGCACCCAACTTTCACTTCTACAGCGTTTGACCAAAATCTTTTGA
ACATAACATTGTAGGGTGTGAAAAAATGCGCACCTTTACCGCTAGCCCAA
GAGGGCACTACAAAATCTAGAGTTGTACTTCAAACGTACATGTAATCCCT
TGTATATACTCGAAAGAAAACATCAAGTTTCTGTATAAATATGAGTGAAA
GCATAATCATACATTATCTTTTCAAAGACGCGTGTACGCATGTAACATTA
TACTGAAAACCTTGCTTGAGAAGGTTTTGG
``` pC10_gal1:alpha-synuclein:barcode:ADHterminator:
guideRNA_expression_cassette

```
GACGCTCGAAGGCTTTAATTTGCGGCCGGTACCCAATTCGCCCTATAGTG
AGTCGTATTACGCGCGCTCACTGGCCGTCGTTTTACAACGTCGTGACTGG
GAAAACCCTGGCGTTACCCAACTTAATCGCCTTGCAGCACATCCCCCTTT
CGCCAGCTGGCGTAATAGCGAAGAGGCCCGCACCGATCGCCCTTCCCAAC
AGTTGCGCAGCCTGAATGGCGAATGGCGCGACGCGCCCTGTAGCGGCGCA
TTAAGCGCGGCGGGTGTGGTGGTTACGCGCAGCGTGACCGCTACACTTGC
CAGCGCCCTAGCGCCCGCTCCTTTCGCTTTCTTCCCTTCCTTTCTCGCCA
CGTTCGCCGGCTTTCCCCGTCAAGCTCTAAATCGGGGGCTCCCTTTAGG
GTTCCGATTTAGTGCTTTACGGCACCTCGACCCCAAAAAACTTGATTAGGG
TGATGGTTCACGTAGTGGGCCATCGCCCTGATAGACGGTTTTTCGCCCTT
TGACGTTGGAGTCCACGTTCTTTAATAGTGGACTCTTGTTCCAAACTGGA
ACAACACTCAACCCTATCTCGGTCTATTCTTTTGATTTATAAGGGATTTT
GCCGATTTCGGCCTATTGGTTAAAAAATGAGCTGATTTAACAAAAATTTA
ACGCGAATTTTAACAAAATATTAACGTTTACAATTTCCTGATGCGGTATT
TTCTCCTTACGCATCTGTGCGGTATTTCACACCGCATAGATCCGTCGAGT
TCAAGAGAAAAAAAAGAAAAAGCAAAAAGAAAAAAGGAAAGCGCGCCTC
GTTCAGAATGACACGTATAGAATGATGCATTACCTTGTCATCTTCAGTAT
CATACTGTTCGTATACATACTTACTGACATTCATAGGTATACATATATAC
ACATGTATATATATCGTATGCTGCAGCTTTAAATAATCGGTGTCACTACA
TAAGAACACCTTTGGTGGAGGGAACATCGTTGGTACCATTGGGCGAGGTG
GCTTCTCTTATGGCAACCGCAAGAGCCTTGAACGCACTCTCACTACGGTG
ATGATCATTCTTGCCTCGCAGACAATCAACGTGGAGGGTAATTCTGCTAG
CCTCTGCAAAGCTTTCAAGAAAATGCGGGATCATCTCGCAAGAGAGATCT
CCTACTTTCTCCCTTTGCAAACCAAGTTCGACAACTGCGTACGGCCTGTT
CGAAAGATCTACCACCGCTCTGGAAAGTGCCTCATCCAAAGGCGCAAATC
CTGATCCAAACCTTTTTACTCCACGCGCCAGTAGGGCCTCTTTAAAAGCT
TGACCGAGAGCAATCCCGCAGTCTTCAGTGGTGTGATGGTCGTCTATGTG
TAAGTCACCAATGCACTCAACGATTAGCGACCAGCCGGAATGCTTGGCCA
GAGCATGCTATCATATGGTCCAGAAACCCTATACCTGTGTGGACGTTAATC
ACTTGCGATTGTGTGGCCTGTTCTGCTACTGCTTCTGCCTCTTTTTCTGG
GAAGATCGAGTGCTCTATCGCTAGGGGACCACCCTTTAAAGAGATCGCAA
TCTGAATCTTGGTTTCATTTGTAATACGCTTTACTAGGGCTTTCTGCTCT
GTCATCTTTGCCTTCGTTTATCTTGCCTGCTCATTTTTTAGTATATTCTT
CGAAGAAATCACATTACTTTATATAATGTATAATTCATTATGTGATAATG
CCAATCGCTAAGAAAAAAAAGAGTCATCCGCTAGGGGAAAAAAAAAAAT
GAAAATCATTACCGAGGCATAAAAAAATATAGAGTGTACTAGAGGAGGCC
AAGAGTAATAGAAAAGAAAATTGCGGGAAAGGACTGTGTTATGACTTCC
CTGACTAATGCCGTGTTCAAACGATACCTGGCAGTGACTCCTAGCGCTCA
CCAAGCTCTTAAAACGGGAATTTATGGTGCACTCTCAGTACAATCTGCTC
TGATGCCGCATAGTTAAGCCAGCCCCGACACCCGCCAACACGCGCTGACG
CGCCCTGACGGGCTTGTCTGCTCCCGGCATCCGCTTACAGACAAGCTGTG
ACCGTCTCCGGGAGCTGCATGTGTCAGAGGTTTTCACCGTCATCACCGAA
ACGCGCGAGACGAAAGGGCCTCGTGATACGCCTATTTTTATAGGTTAATG
TCATGATAATAATGGTTTCTTAGGACGGATCGCTTGCCTGTAACTTACAC
```

Supplemental Sequences:

```
GCGCCTCGTATCTTTTAATGATGGAATAATTTGGGAATTTACTCTGTTT
TATTTATTYTTATGTTTTGTATTTGGATTTTAGAAAGTAAATAAAGAAGG
TAGAAGAGTTACGGAATGAAGAAAAAAAAATAAACAAAGGTTTAAAAAAT
TTCAACAAAAAGCGTACTTTACATATATATTTATTAGACAAGAAAAGCAG
ATTAAATAGATATACATTCGATTAACGATAAGTAAAATGTAAAATCACAG
GATTTTCGTGTGTGGTCTTCTACACAGACAAGATGAAACAATTCGGCATT
AATACCTGAGAGCAGGAAGAGCAAGATAAAAGGTAGTATTTGTTGGCGAT
CCCCCTAGAGTCTTTTACATCTTCGGAAAACAAAAACTATTTTTTCTTTA
ATTTCTTTTTTTACTTTCTATTTTTAATTTATATATTTATATTAAAAAAT
TTAAATTATAATTATTTTTATAGCACGTGATGAAAAGGACCCAGGTGGCA
CTTTTCGGGGAAATGTGCGCGGAACCCCTATTTGTTTATTTTTCTAAATA
CATTCAAATATGTATCCGCTCATGAGACAATAACCCTGATAAATGCTTCA
ATAATATTGAAAAAGGAAGAGTATGAGTATTCAACATTTCCGTGTCGCCC
TTATTCCCTTTTTTGCGGCATTTTGCCTTCCTGTTTTTGCTCACCCAGAA
ACGCTGGTGAAAGTAAAAGATGCTGAAGATCAGTTGGGTGCACGAGTGGG
TTACATCGAACTGGATCTCAACAGCGGTAAGATCCTTGAGAGTTTTCGCC
CCGAAGAACGTTTTCCAATGATGAGCACTTTTAAAGTTCTGCTATGTGGC
GCGGTATTATCCCGTATTGACGCCGGGCAAGAGCAACTCGGTCGCCGCAT
ACACTATTCTCAGAATGACTTGGTTGAGTACTCACCAGTCACAGAAAAGC
ATCTTACGGATGGCATGACAGTAAGAGAATTATGCAGTGCTGCCATAACC
ATGAGTGATAACACTGCGGCCAACTTACTTCTGACAACGATCGGAGGACC
GAAGGAGCTAACCGCTTYTTTGCACAACATGGGGGATCATGTAACTCGCC
TTGATCGTTGGGAACCGGAGCTGAATGAAGCCATACCAAACGACGAGCGT
GACACCACGATGCCTGTAGCAATGGCAACAACGTTGCGCAAACTATTAAC
TGGCGAACTACTTACTCTAGCTTCCCGGCAACAATTAATAGACTGGATGG
AGGCGGATAAAGTTGCAGGACCACTTCTGCGCTCGGCCCTTCCGGCTGGC
TGGTTTATTGCTGATAAATCTGGAGCCGGTGAGCGTGGGTCTCGCGGTAT
CATTGCAGCACTGGGGCCAGATGGTAAGCCCTCCCGTATCGTAGTTATCT
ACACGACGGGGAGTCAGGCAACTATGGATGAACGAAATAGACAGATCGCT
GAGATAGGTGCCTCACTGATTAAGCATTGGTAACTGTCAGACCAAGTTTA
CTCATATATACTTTAGATTGATTTAAAACTTCATTTTTAATTTAAAAGGA
TCTAGGTGAAGATCCTTTTTGATAATCTCATGACCAAAATCCCTTAACGT
GAGTTTTCGTTCCACTGAGCGTCAGACCCCGTAGAAAAGATCAAAGGATC
TTCTTGAGATCCTTTTTTTCTGCGCGTAATCTGCTGCTTGCAAACAAAAA
AACCACCGCTACCAGCGGTGGTTTGTTTGCCGGATCAAGAGCTACCAACT
CTTTTTCCGAAGGTAACTGGCTTCAGCAGAGCGCAGATACCAAATACTGT
CCTTCTAGTGTAGCCGTAGTTAGGCCACCACTTCAAGAACTCTGTAGCAC
CGCCTACATACCTCGCTCTGCTAATCCTGTTACCAGTGGCTGCTGCCAGT
GGCGATAAGTCGTGTCTTACCGGGTTGGACTCAAGACGATAGTTACCGGA
TAAGGCGCAGCGGTCGGGCTGAACGGGGGGTTCGTGCACACAGCCCAGCT
TGGAGCGAACGACCTACACCGAACTGAGATACCTACAGCGTGAGCTATGA
GAAAGCGCCACGCTTCCCGAAGGGAGAAAGGCGGACAGGTATCCGGTAAG
CGGCAGGGTCGGAACAGGAGAGCGCACGAGGGAGCTTCCAGGGGGAAACG
CCTGGTATCTTTATAGTCCTGTCGGGTTTCGCCACCTCTGACTTGAGCGT
CGATTTTTGTGATGCTCGTCAGGGGGCGGAGCCTATGGAAAAACGCCAG
CAACGCGGCCTTTTTACGGTTCCTGGCCTTTTGCTGGCCTTTTGCTCACA
TGTTCTTTCCTGCGTTATCCCCTGATTCTGTGGATAACCGTATTACCGCC
TTTGAGTGAGCTGATACCGCTCGCCGCAGCCGAACGACCGAGCGCAGCGA
GTCAGTGAGCGAGGAAGCGGAAGAGCGCCCAATACGCAAACCGCCTCTCC
CCGCGCGTTGGCCGATTCATTAATGCAGCTGGCACGACAGGTTTCCCGAC
TGGAAAGCGGGCAGTGAGCGCAACGCAATTAATGTGAGTTACCTCACTCA
TTAGGCACCCCAGGCTTTACACTTTATGCTTCCGGCTCCTATGTTGTGTG
GAATTGTGAGCGGATAACAATTTCACACAGGAAACAGCTATGACCATGAT
TACGCCAAGCGCGCAATTAACCCTCACTAAAGGGAACAAAAGCTGGAGCT
CTAGTACGGATTAGAAGCCGCCGAGCGGGCGACAGCCCTCCGACGGAAGA
CTCTCCTCCGTGCGTCCTCGTCTTCACCGGTCGCGTTCCTGAAACGCAGA
TGTGCCTCGCGCCGCACTGCTCCGAACAATAAAGATTCTACAATACTAGC
TTTTATGGTTATGAAGAGGAAAATTGGCAGTAACCTGGCCCCACAAACC
TTCAAATTAACGAATCAAATTAACAACCATAGGATGATAATGCGATTAGT
TTTTTAGCCTTATTTCTGGGGTAATTAATCAGCGAAGCGATGATTTTTGA
TCTATTAACAGATATATAAATGGAAAAGCTGCATAACCACTTTAACTAAT
ACTTTCAACATTTTCAGTTTGTATTACTTCTTATTCAAATGTCATAAAAG
TATCAACAAAAAATTGTTAATATACCTCTATACTTTAACGTCAAGGAGAA
AAAACCCCGGATTCTAGAAAAATGGATGTATTCATGAAAGGACTTTCAAA
GGCCAAGGAGGGAGTTGTGGCTGCTGCTGAGAAAACCAAACAGGGTGTGG
CAGAAGCAGCAGGAAAGACAAAAGAGGGTGTTCTCTATGTAGGCTCCAAA
ACCAAGGAGGGAGTGGTGCATGGTGTGACAACAGTGGCTGAGAAGACCAA
AGAGCAAGTGACAAATGTTGGAGGAGCAGTGGTGACGGGTGTGACAGCAG
TAGCCCAGAAGACAGTGGAGGGAGCAGGGAGCATTGCAGCAGCCACTGGC
TTTGTCAAAAAGGACCAGTTGGGCAAGAATGAAGAAGGAGCCCCACAGGA
AGGAATTCTGGAAGATATGCCTGTGGATCCTGACAATGAGGCTTATGAAA
TGCCTTCTGAGGAAGGGTATCAAGACTACGAACCTGAAGCCTAATAATGG
TCATGTGCCGAACTGGTGCGAAAAATCGATGCGAATTTCTTATGATTTAT
GATTYTTATTATTAAATAAGTTATAAAAAAATAAGTGTATACAAATTTT
AAAGTGACTCTTAGGTTTTAAAACGAAAATTCTTAAGACATAAAAACAA
AAAAAGCACCACCGACTCGGTGCCACTTTTTCAAGTTGATAACGGACTAG
CCTTATTTTAACTTGCTATTTCTAGCTCTAAAACCGAGACGCATTAATCG

TCTCGGATCATTTATCTTTCACTGCGGAGAAGTTTCGAACGCCGAAACAT
GCGCACCAACTTTCACTTCTACAGCGTTTGACCAAAATCTTTTGAACATA
ACATTGTAGGGTGTGAAAAAATGCGCACCTTTACCGCTAGCCCAAGAGGG
CACTACAAAATCTAGAGTTGTACTTCAAACGTACATGTAATCCCTTGTAT
ATACTCGAAAGAAAACATCAAGTTTCTGTATAAATATGAGTGAAAGCATA
ATCATACATTATCTTTTCAAAGACGCGTGTACGCATGTAACATTATACTG
AAAACCTTGCTTGAGAAGGTTTTGG
```

EXAMPLE V

Cas/Guide RNA Genome Editing as a Perturbation of an Altered Yeast Strain

The present disclosure provides methods of screening genetic perturbations for their ability to inhibit the toxic effect of a protein on an altered yeast strain within a plurality of altered yeast strains. The genetic perturbation is carried out using a RNA-guided DNA binding protein, such as a Cas/guide RNA genome editing approach as is known in the art. A library of plasmids are created with each including an endogenous or exogenous gene which encodes an endogenous or exogenous protein, i.e. a toxic protein, a guide RNA having a spacer sequence complementary to a target nucleic acid sequence, and a barcode associated with the endogenous/exogenous protein and the guide RNA. An endogenous gene or protein is one that is native to the cell, i.e., is naturally occurring within the cell. An exogenous gene or protein is one that is not native to the cell, i.e. it is not naturally occurring within the cell, for example by it being a foreign gene that is introduced into the cell to produce a foreign protein. Yeast is transformed with the library of plasmids, the endogenous gene is expressed and the phenotype of slowed growth or proliferation is observed. The guide RNA and an RNA-guided DNA binding protein, such as a Cas enzyme for example, form a colocalization complex at a target nucleic acid, and the target nucleic acid is modulated or cut or nicked to provide the genetic permutation. After a proliferation period, the relative abundance of the barcodes is analyzed, such as by next generation sequencing, and correlated with the endogenous gene, the guide RNA and the target nucleic acid which has been modulated, cut or nicked. Instances are detected where a given barcode associated with a toxic protein and a guide RNA changing the expression of a target endogenous gene within yeast are represented more or less than the average. For those barcodes with an increased abundance or which are more highly represented, the genetic permutation caused by the modulation, nicking or cutting of the target nucleic acid is deemed to have inhibited the toxic effect of the endogenous protein, i.e. has increased tolerance towards the toxic gene being analyzed. For those barcodes with a decreased abundance or which are less highly represented, the genetic permutation caused by the modulation, nicking or cutting of the target nucleic acid is deemed to have improved the toxic effect of the endogenous protein, i.e. has increased sensitivity towards the toxic gene being analyzed. In this manner, plasmids can be created which include guide RNA to target any nucleic acid in the yeast cell thereby providing a method of multiplexing the screening of genetic permutations for the ability to rescue a cell from the toxic effect of an exogenous protein or several or a plurality of exogenous proteins within the pool of cells.

Figure 6:
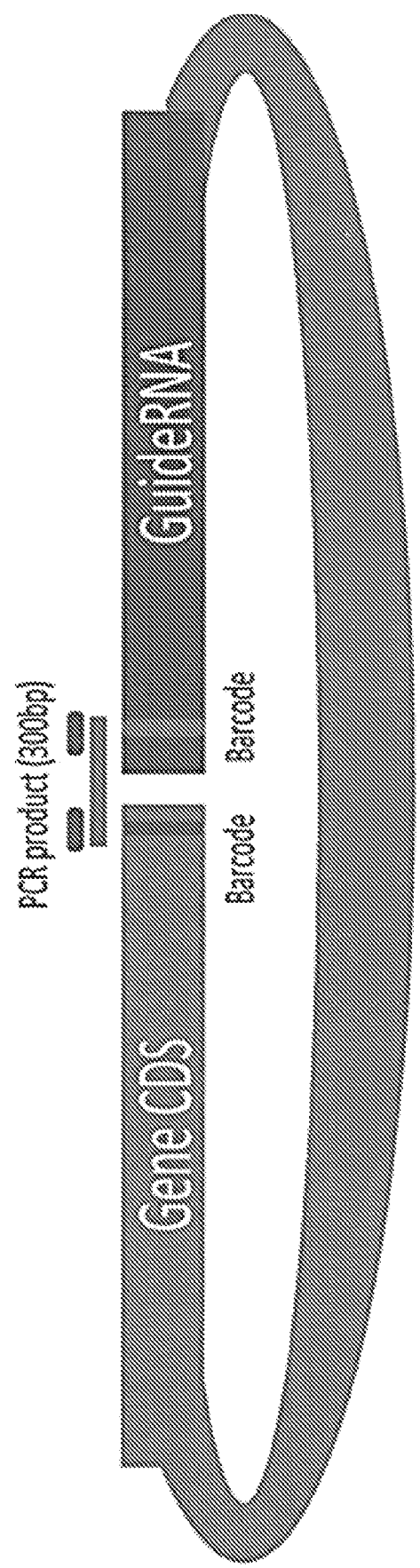
FIG. 6 is an illustration of a plasmid including a nucleic acid encoding a disease causing gene, a barcode associated with the disease causing gene and a guide RNA associated with a target nucleic acid.

FIG. 6 illustrates a plasmid including a nucleic acid sequence encoding an exogenous disease causing gene, a barcode unique to the exogenous disease causing gene and a guide RNA. A PCR product including the barcode and the guide RNA is produced and sequenced to identify the barcode, and thus the gene of interest, as well as the guide RNA (which may also serve as a barcode), and thus the target nucleic acid.

Figure 7:
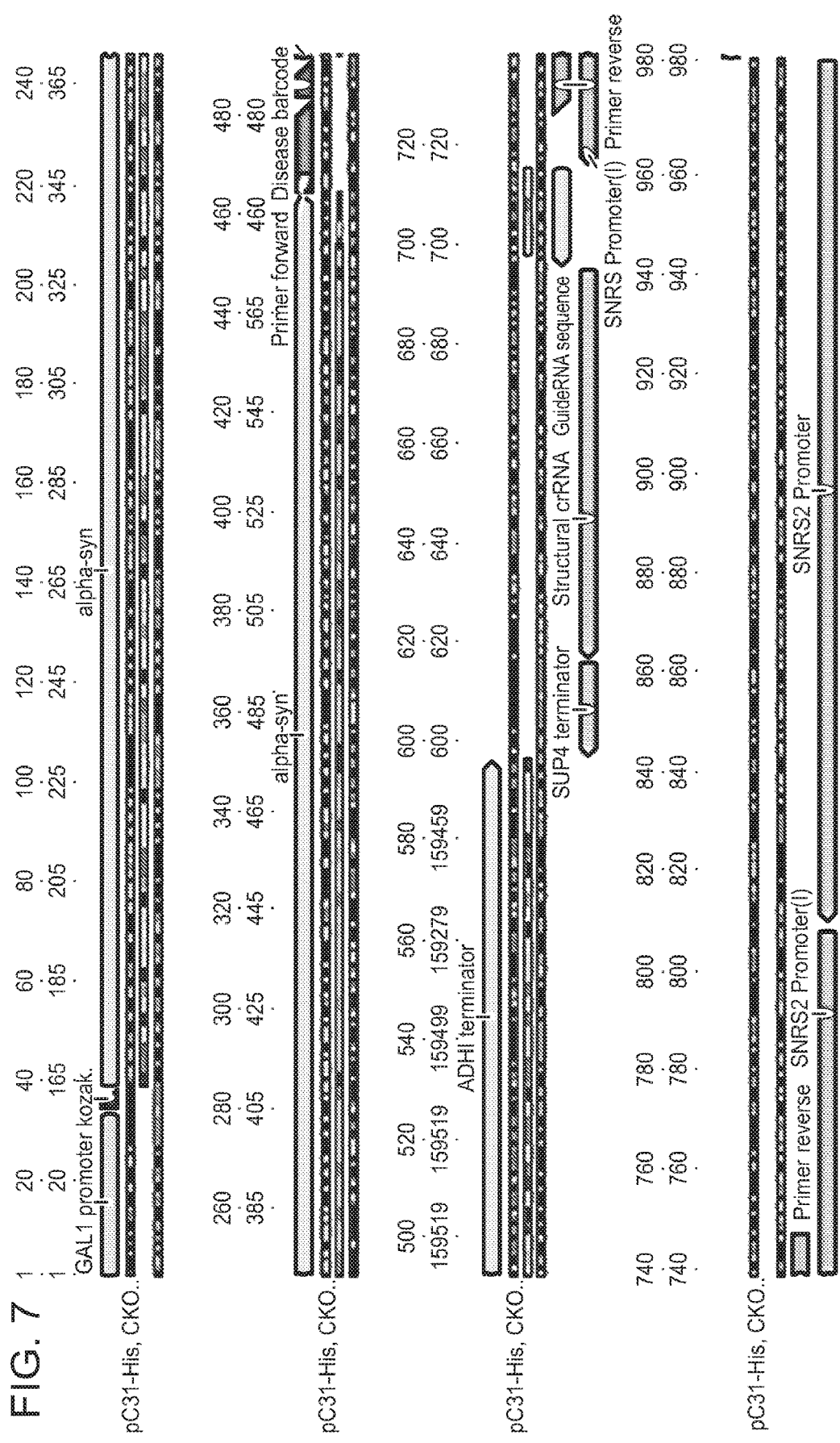
FIG. 7 is a schematic of a dual barcode detection system.

FIG. 7 illustrates a nucleic acid sequence encoding an exogenous disease causing gene, a barcode unique to the exogenous disease causing gene and a guide RNA. In particular, nucleic acid sequence encodes a disease causing gene (alpha-synuclein) under the control of an inducible promoter. The gene is flanked downstream by a primer binding site followed by a gene specific barcode, a minimal gene terminator and then a guideRNA expression cassette in the minus orientation. By amplifying the sequence between the two primers (283 bp) both the gene barcode and the guideRNA can be sequenced allowing the user to couple the disease causing gene and the guideRNA that ameliorates the disease allowing the cell to grow. Accordingly, the genetic construct allows one to amplify out a single contiguous piece of DNA and from that amplicon determine what exogenous gene is being expressed and what genetic perturbation is being performed by the Cas enzyme to alter the effect of expressing the exogenous gene of interest.

According to certain aspects, the RNA guided DNA binding protein can be provided to a cell by genetically modifying the cell to include a nucleic acid encoding the RNA guided DNA binding protein or otherwise providing a vector or plasmid encoding the RNA guided DNA binding protein wherein the nucleic acid is expressed to produce the RNA guided DNA binding protein. The RNA guided DNA binding protein may also be provided to the cell as a native protein, i.e. not as a product of expression of a nucleic acid sequence. Methods of providing an RNA guided DNA binding protein to a cell are known in the art.

Exemplary RNA-Guided DNA Binding Proteins

The RNA-guided DNA binding protein includes an RNA-guided DNA binding protein nuclease, a thermophilic RNA-guided DNA binding protein nuclease, an RNA-guided DNA binding protein nickase, or a nuclease null RNA-guided DNA binding protein. According to one aspect, the RNA-guided DNA binding protein includes a Cas nuclease, a Cas nickase or a nuclease null Cas protein. A Cas nickase or a nuclease-null Cas protein is provided where one or more amino acids in Cas, such as Cas9, are altered or otherwise removed to provide a Cas nickase or a nuclease null Cas protein. According to one aspect, the amino acids include D10 and H840 of Cas9. See Jinek et al., *Science* 337, 816-821 (2012). RNA guided DNA binding proteins are readily known to those of skill in the art to bind to DNA for various purposes. Such DNA binding proteins may be naturally occurring. DNA binding proteins having nuclease activity are known to those of skill in the art, and include naturally occurring DNA binding proteins having nuclease activity, such as Cas9 proteins present, for example, in Type II CRISPR systems. Such Cas9 proteins and Type II CRISPR systems are well documented in the art. See Makarova et al., *Nature Reviews, Microbiology*, Vol. 9, June 2011, pp. 467-477 including all supplementary information hereby incorporated by reference in its entirety.

A Cas as described herein may be any Cas known to those of skill in the art that may be directed to a target nucleic acid using an RNA as known to those of skill in the art. The Cas may be wild type or a homolog or ortholog thereof, such as Cpf1 (See, Zetsche, Bernd et al., Cpf1 Is a Single RNA-Guided Endonuclease of a Class 2 CRISPR-Cas System, *Cell*, Volume 163, Issue 3, pgs 759-771, hereby incorporated by reference in its entirety). The Cas may be nonnaturally occurring, such as an engineered Cas as disclosed in Slaymaker, I. M., Gao, L., Zetsche, B., Scott, D. A., Yan, W. X. and Zhang, F., 2016. Rationally engineered Cas9 nucleases with improved specificity. *Science*, 351(6268), pp. 84-88 hereby incorporated by reference in its entirety. The Cas may have one or more nucleolytic domains altered to prevent nucleolytic activity, such as with a Cas nickase or nuclease null or "dead" Cas. Aspects of the present disclosure utilize nicking to effect cutting of one strand of the target nucleic acid. A nuclease null or "dead" Cas may have a nuclease attached thereto to effect cutting, cleaving or nicking of the target nucleic acid. Such nucleases are known to those of skill in the art.

According to one aspect, the RNA-guided DNA binding protein includes a Cas9 nuclease, a Cas9 nickase or a nuclease null Cas9 protein. According to one aspect, the RNA-guided DNA binding protein includes a spCas9 nuclease, a spCas9 nickase or a nuclease null spCas9 protein. According to one aspect, the RNA-guided DNA binding proteins includes *S. pyogenes* Cas9, *S. thermophilis* Cas9, *N. meningitides* Cas9, *T. denticola* Cas9, or *S. aureus* Cas9. According to one aspect, the RNA-guided DNA binding protein includes a Cpf1 nuclease, a Cpf1 nickase or a nuclease null Cpf1 protein.

According to one aspect, the Cas9 protein, Cas9 protein nickase or nuclease null Cas9 includes homologs and orthologs thereof which retain the ability of the protein to bind to the DNA and be guided by the RNA. According to one aspect, the Cas9 protein includes the sequence as set forth for naturally occurring Cas9 from *S. thermophiles* or *S. pyogenes* or *N. meningitides* or *T. denticola* or *S. aureus* or Cpf1 or NgAgo or C2C2 or protein sequences having at least 30%, 40%, 50%, 60%, 70%, 80%, 90%, 95%, 98% or 99% homology thereto and being a DNA binding protein, such as an RNA guided DNA binding protein.

An exemplary CRISPR system includes the *S. thermophiles* Cas9 nuclease (ST1 Cas9) (see Esvelt K M, et al., Orthogonal Cas9 proteins for RNA-guided gene regulation and editing, *Nature Methods*., (2013) hereby incorporated by reference in its entirety). An exemplary CRISPR system includes the *S. pyogenes* Cas9 nuclease (Sp. Cas9), an extremely high-affinity (see Sternberg, S. H., Redding, S., Jinek, M., Greene, E. C. & Doudna, J. A. DNA interrogation by the CRISPR RNA-guided endonuclease Cas9. *Nature* 507, 62-67 (2014) hereby incorporated by reference in its entirety), programmable DNA-binding protein isolated from a type II CRISPR-associated system (see Garneau, J. E. et al. The CRISPR/Cas bacterial immune system cleaves bacteriophage and plasmid DNA. *Nature* 468, 67-71 (2010) and Jinek, M. et al. A programmable dual-RNA-guided DNA endonuclease in adaptive bacterial immunity. *Science* 337, 816-821 (2012) each of which are hereby incorporated by reference in its entirety). According to certain aspects, a nuclease null or nuclease deficient Cas 9 can be used in the methods described herein. Such nuclease null or nuclease deficient Cas9 proteins are described in Gilbert, L. A. et al. CRISPR-mediated modular RNA-guided regulation of transcription in eukaryotes. *Cell* 154, 442-451 (2013); Mali, P. et al. CAS9 transcriptional activators for target specificity screening and paired nickases for cooperative genome engineering. *Nature biotechnology* 31, 833-838 (2013); Maeder, M. L. et al. CRISPR RNA-guided activation of endogenous human genes. *Nature methods* 10, 977-979 (2013); and Perez-Pinera, P. et al. RNA-guided gene activation by CRISPR-Cas9-based transcription factors. *Nature methods* 10, 973-976 (2013) each of which are hereby incorporated by reference in its entirety. The DNA locus targeted by Cas9 (and by its nuclease-deficient mutant, "dCas9" precedes a three nucleotide (nt) 5"-NGG-3' "PAM" sequence, and matches a 15-22-nt guide or spacer sequence within a Cas9-bound RNA cofactor, referred to herein and in the art as a guide RNA. Altering this guide RNA is sufficient to target Cas9 or a nuclease deficient Cas9 to a target nucleic acid. In a multitude of CRISPR-based biotechnology applications (see Mali, P., Esvelt, K. M. & Church, G. M. Cas9 as a versatile tool for engineering biology. *Nature methods* 10, 957-963 (2013); Hsu, P. D., Lander, E. S. & Zhang, F. Development and Applications of CRISPR-Cas9 for Genome Engineering. *Cell* 157, 1262-1278 (2014); Chen, B. et al. Dynamic imaging of genomic loci in living human cells by an optimized CRISPR/Cas system. *Cell* 155, 1479-1491 (2013); Shalem, O. et al. Genome-scale CRISPR-Cas9 knockout screening in human cells. *Science* 343, 84-87 (2014); Wang, T., Wei, J. J., Sabatini, D. M. & Lander, E. S. Genetic screens in human cells using the CRISPR-Cas9 system. *Science* 343, 80-84 (2014); Nissim, L., Perli, S. D., Fridkin, A., Perez-Pinera, P. & Lu, T. K. Multiplexed and Programmable Regulation of Gene Networks with an Integrated RNA and CRISPR/Cas Toolkit in Human Cells. *Molecular cell* 54, 698-710 (2014); Ryan, O. W. et al. Selection of chromosomal DNA libraries using a multiplex CRISPR system. *eLife* 3 (2014); Gilbert, L. A. et al. Genome-Scale CRISPR-Mediated Control of Gene Repression and Activation. Cell (2014); and Citorik, R. J., Mimee, M. & Lu, T. K. Sequence-specific antimicrobials using efficiently delivered RNA-guided nucleases. *Nature biotechnology* (2014) each of which are hereby incorporated by reference in its entirety), the guide is often presented in a so-called sgRNA (single guide RNA), wherein the two natural Cas9 RNA cofactors (gRNA and tracrRNA) are fused via an engineered loop or linker.

Cas9 proteins are known to exist in many Type II CRISPR systems including the following as identified in the supplementary information to Makarova et al., Nature Reviews, Microbiology, Vol. 9, June 2011, pp. 467-477: Methanococcus maripaludis C7; *Corynebacterium diphtheriae; Corynebacterium efficiens* YS-314; *Corynebacterium glutamicum* ATCC 13032 Kitasato; *Corynebacterium glutamicum* ATCC 13032 Bielefeld; *Corynebacterium glutamicum* R; *Corynebacterium kroppenstedtii* DSM 44385; *Mycobacterium abscessus* ATCC 19977; *Nocardia farcinica* IFM10152; *Rhodococcus erythropolis* PR4; *Rhodococcus jostii* RHA1; *Rhodococcus opacus* B4 uid36573; *Acidothermus cellulolyticus* 11B; *Arthrobacter chlorophenolicus* A6; *Kribbella flavida* DSM 17836 uid43465; *Thermomonospora curvata* DSM 43183; *Bifidobacterium dentium* Bd1; *Bifidobacterium longum* DJO10A; *Slackia heliotrinireducens* DSM 20476; *Persephonella marina* EX H1; *Bacteroides fragilis* NCTC 9434; *Capnocytophaga ochracea* DSM 7271; *Flavobacterium psychrophilum* JIP02 86; *Akkermansia muciniphila* ATCC BAA 835; *Roseiflexus castenholzii* DSM 13941; *Roseiflexus* RS1; *Synechocystis* PCC6803; *Elusimicrobium minutum* Pei191; uncultured Termite group 1 bacterium phylotype Rs D17; *Fibrobacter succinogenes* S85; *Bacillus cereus* ATCC 10987; *Listeria innocua; Lactobacillus casei; Lactobacillus rhamnosus* GG; *Lactobacillus salivarius* UCC118; *Streptococcus agalactiae* A909; *Streptococcus agalactiae* NEM316; *Streptococcus agalactiae* 2603; *Streptococcus dysgalactiae equisimilis* GGS 124; *Streptococcus equi zooepidemicus* MGCS10565; *Streptococcus gallolyticus* UCN34 uid46061; *Streptococcus gordonii* Challis subst CH1; *Streptococcus mutans* NN2025 uid46353; *Streptococcus mutans; Streptococcus pyogenes* M1 GAS; *Streptococcus pyogenes* MGAS5005; *Streptococcus pyogenes* MGAS2096; *Streptococcus pyogenes* MGAS9429; *Streptococcus pyogenes* MGAS10270; *Streptococcus pyogenes* MGAS6180; *Streptococcus pyogenes* MGAS315; *Streptococcus pyogenes* SSI-1; *Streptococcus pyogenes* MGAS10750; *Streptococcus pyogenes* NZ 131; *Streptococcus thermophiles* CNRZ1066; *Streptococcus thermophiles* LMD-9; *Streptococcus thermophiles* LMG 18311; *Clostridium botulinum* A3 Loch Maree; *Clostridium botulinum* B Eklund 17B; *Clostridium botulinum* Ba4 657; *Clostridium botulinum* F Langeland; *Clostridium cellulolyticum* H10; *Finegoldia magna* ATCC 29328; *Eubacterium rectale* ATCC 33656; *Mycoplasma gallisepticum; Mycoplasma mobile* 163K; *Mycoplasma penetrans; Mycoplasma synoviae* 53; *Streptobacillus moniliformis* DSM 12112; *Bradyrhizobium* BTAi1; *Nitrobacter hamburgensis* X14; *Rhodopseudomonas palustris* BisB18; *Rhodopseudomonas palustris* BisB5; *Parvibaculum lavamentivorans* DS-1; *Dinoroseobacter shibae* DFL 12; *Gluconacetobacter diazotrophicus* Pal 5 FAPERJ; *Gluconacetobacter diazotrophicus* Pal 5 JGI; *Azospirillum* B510 uid46085; *Rhodospirillum rubrum* ATCC 11170; *Diaphorobacter* TPSY uid29975; *Verminephrobacter eiseniae* EF01-2; *Neisseria meningitides* 053442; *Neisseria meningitides* alpha14; *Neisseria meningitides* Z2491; *Desulfovibrio salexigens* DSM 2638; *Campylobacter jejuni* doylei 269 97; *Campylobacter jejuni* 81116; *Campylobacter jejuni; Campylobacter lari* RM2100; *Helicobacter hepaticus; Wolinella succinogenes; Tolumonas auensis* DSM 9187; *Pseudoalteromonas atlantica* T6c; *Shewanella pealeana* ATCC 700345; *Legionella pneumophila* Paris; *Actinobacillus succinogenes* 130Z; *Pasteurella multocida; Francisella tularensis novicida* U112; *Francisella tularensis* holarctica; *Francisella tularensis* FSC 198; *Francisella tularensis tularensis; Francisella tularensis* WY96-3418; and *Treponema denticola* ATCC 35405. The Cas9 protein may be referred by one of skill in the art in the literature as Csn1. An exemplary *S. pyogenes* Cas9 protein sequence is provided in Deltcheva et al., *Nature* 471, 602-607 (2011) hereby incorporated by reference in its entirety.

Modification to the Cas protein is a representative embodiment of the present disclosure. CRISPR systems useful in the present disclosure are described in R. Barrangou, P. Horvath, CRISPR: new horizons in phage resistance and strain identification. *Annual review of food science and technology* 3, 143 (2012) and B. Wiedenheft, S. H. Sternberg, J. A. Doudna, RNA-guided genetic silencing systems in bacteria and archaea. *Nature* 482, 331 (Feb. 16, 2012) each of which are hereby incorporated by reference in their entireties.

According to one aspect, the RNA-guided DNA binding protein includes an effector moiety or group attached thereto to affect or alter or modulate a target nucleic acid. The RNA-guided DNA binding protein may be a nuclease null RNA-guided DNA binding protein including an effector moiety or group attached thereto. An effector moiety or group includes a modulator moiety or group. Modulating may refer to the function of the effector group or moiety attached to the RNA-guided DNA binding protein or guide RNA. A target nucleic acid may be modulated by being cut or nicked by the RNA-guided DNA binding protein. A target nucleic acid may be modulated by being bound by the RNA-guided DNA binding protein. A target nucleic acid may be modulated by the function of the effector group or moiety attached to the RNA-guided DNA binding protein or the guide RNA. A target nucleic acid may be modulated by being bound by the RNA-guided DNA binding protein and the function of the effector group or moiety attached to the RNA-guided DNA binding protein or the guide RNA.

Additional exemplary RNA-guided DNA binding proteins includes Cas9 proteins include Cas9 proteins attached to, bound to or fused or connected or tethered with a functional protein or effector group or modulator such as transcriptional regulators, such as transcriptional activators or repressors, a Fok-domain, such as Fok 1, an aptamer, a binding protein, PP7, MS2 and the like. The nuclease null Cas9 protein and the guide RNA colocalize to the target nucleic acid or the nucleic acid encoding the guide RNA resulting in binding but not cleaving of the target nucleic acid. The activity or transcription of the target nucleic acid is regulated by such binding. The Cas9 protein can further comprise a transcriptional regulator or DNA modifying protein attached thereto. According to one aspect, the transcriptional regulator protein or domain is a transcriptional activator. According to one aspect, the transcriptional regulator protein or domain upregulates expression of the target nucleic acid. According to one aspect, the transcriptional regulator protein or domain is a transcriptional repressor. According to one aspect, the transcriptional regulator protein or domain downregulates expression of the target nucleic acid. Transcriptional activators and transcriptional repressors can be readily identified by one of skill in the art based on the present disclosure. Exemplary transcriptional regulators are known to a skilled in the art and include VPR, VP16, VP64, P65 and RTA. See Zhang et al., *Nature Biotechnology* 29, 149-153 (2011) hereby incorporated by reference in its entirety. The transcriptional regulatory domains correspond to targeted loci. Accordingly, aspects of the present disclosure include methods and materials for localizing transcriptional regulatory domains to targeted loci of target nucleic acids by fusing, connecting or joining such domains to an RNA-guided DNA binding protein such as Cas or a guide RNA.

Exemplary effector groups or moieties include a detectable moiety, a transcriptional regulator, a protein domain, a nuclease, a phosphatase, deaminase, kinase, polynucleotide kinase, Uracil-DNA glycosylase, nuclease, endonuclease, exonuclease, site-specific nuclease, ligase, polymerase, recombinase, methyl-transferase, fluorescent protein, beta-galactosidase, antibody, scFv single-chain variable fragment of an antibody, nanobody, transcriptional activator, transcriptional repressor, biotin, streptavidin, aptamer, nanoparticle, gold nanoparticle, quantum dot, magnetic bead, paramagnetic particle, or oligonucleotide. Exemplary DNA-modifying enzymes are known to a skilled in the art and include Cytidine deaminases, APOBECs, Fok1, endonucleases and DNases.

Exemplary Guide RNA

Embodiments of the present disclosure are directed to the use of a RNA-guided DNA binding protein/guide RNA system, such as a CRISPR/Cas system and, in particular, a guide RNA which may include one or more of a spacer sequence, a tracr mate sequence and a tracr sequence. The term spacer sequence is understood by those of skill in the art and may include any polynucleotide having sufficient complementarity with a target nucleic acid sequence to hybridize with the target nucleic acid sequence and direct sequence-specific binding of a CRISPR complex to the target sequence. According to certain aspects, an exemplary spacer sequence is between 10 and 30 nucleotides in length. According to certain aspects, an exemplary spacer sequence is between 15 and 25 nucleotides in length. An exemplary spacer sequence is between 18 and 22 nucleotides in length. An exemplary spacer sequence is 20 nucleotides in length.

The guide RNA may be formed from a spacer sequence covalently connected to a tracr mate sequence (which may be referred to as a crRNA) and a separate tracr sequence, wherein the tracr mate sequence is hybridized to a portion of the tracr sequence. According to certain aspects, the tracr mate sequence and the tracr sequence are connected or linked such as by covalent bonds by a linker sequence, which construct may be referred to as a fusion of the tracr mate sequence and the tracr sequence. The linker sequence referred to herein is a sequence of nucleotides, referred to herein as a nucleic acid sequence, which connect the tracr mate sequence and the tracr sequence. Accordingly, a guide RNA may be a two component species (i.e., separate crRNA and tracr RNA which hybridize together) or a unimolecular species (i.e., a crRNA-tracr RNA fusion, often termed an sgRNA).

Tracr mate sequences and tracr sequences are known to those of skill in the art, such as those described in US 2014/0356958 and as shown in FIG. 2. An exemplary tracr mate sequence and tracr sequence is N20 to N8-gtatagagctagaaatagcaagttaaaataaggctagtccgttatcaactt-gaaaaagtggcaccgagtcggtgcttttttt with N20-8 being the number of nucleotides complementary to a target locus of interest. According to certain aspects, the tracr mate sequence is between about 17 and about 27 nucleotides in length. According to certain aspects, the tracr sequence is between about 65 and about 75 nucleotides in length. According to certain aspects, the linker nucleic acid sequence is between about 4 and about 6. According to certain methods, two or more or a plurality of guide RNAs may be used in the practice of certain embodiments. According to certain aspects, the guide RNA is between about 10 to about 500 nucleotides. According to one aspect, the guide RNA is between about 20 to about 100 nucleotides. According to certain aspects, the spacer sequence is between about 10 and about 500 nucleotides in length and particularly between about 14 and about 22 nucleotides in length. According to certain aspects, the tracr mate sequence is between about 10 and about 500 nucleotides in length. According to certain aspects, the tracr sequence is between about 10 and about 100 nucleotides in length. According to certain aspects, the linker nucleic acid sequence is between about 4 and about 100 nucleotides in length, and particularly between about 4 and about 6 nucleotides in length.

According to one aspect, the guide RNA includes an effector moiety or group attached thereto. An effector moiety or group includes a modulator moiety or group. Exemplary effector groups or moieties include a detectable moiety, a transcriptional regulator, a protein domain, a nuclease, a phosphatase, deaminase, kinase, polynucleotide kinase, Uracil-DNA glycosylase, nuclease, endonuclease, exonuclease, site-specific nuclease, ligase, polymerase, recombinase, methyl-transferase, fluorescent protein, beta-galactosidase, antibody, scFv single-chain variable fragment of an antibody, nanobody, transcriptional activator, transcriptional repressor, biotin, streptavidin, aptamer, nanoparticle, gold nanoparticle, quantum dot, magnetic bead, paramagnetic particle, or oligonucleotide.

Exemplary Target Nucleic Acid

Target nucleic acids as described herein include any nucleic acid sequence to which a co-localization complex as described herein can be useful to either cut, nick or regulate or modulate. Target nucleic acids include nucleic acid sequences, such as genomic nucleic acids, such as genes, capable of being expressed into proteins. For purposes of the present disclosure, a co-localization complex can bind to or otherwise co-localize with the target nucleic acid at or adjacent or near the target nucleic acid and in a manner in which the co-localization complex may have a desired effect on the target nucleic acid. One of skill based on the present disclosure will readily be able to identify or design guide RNAs and Cas9 proteins which co-localize to a target nucleic acid. One of skill will further be able to identify effector groups or modulators or transcriptional regulator proteins or domains which likewise co-localize to a target nucleic acid.

The invention claimed is:

1. A method of screening comprising
providing a combination of a plurality of proliferating cell types wherein each proliferating cell type has a unique associated barcode within its genome that is different from other proliferating cell types of the plurality and wherein each proliferating cell type includes an exogenous gene present on a plasmid that when expressed produces an associated phenotype to the proliferating cell type which alters proliferation of the cell type,
introducing a perturbation to one or more of the plurality of proliferating cell types,
inducing expression of one or more of the exogenous genes,
determining the relative number of unique associated barcodes after a period of proliferation, and
comparing the relative number of unique associated barcodes to a control relative number of unique associated barcodes to indicate the effect of the perturbation on the one or more of the plurality of proliferating cell types.

2. The method of claim 1 wherein expression of the exogenous gene produces an associated phenotype to the proliferating cell type which reduces proliferation of the cell type.

3. The method of claim 1 wherein the exogenous gene is a toxicity gene that when expressed causes toxicity to the proliferating cell type thereby reducing proliferation of the proliferating cell type.

4. The method of claim 3 wherein the exogenous gene encodes an aggregation prone protein hnRNPA1 or FUS.

5. The method of claim 1 wherein the perturbation is a chemical perturbation.

6. The method of claim 1 wherein the perturbation is a genetic perturbation.

7. The method of claim 1 wherein the control relative number of unique associated barcodes is determined by providing a combination of a plurality of proliferating cell types wherein each proliferating cell type has a unique associated barcode that is different from other proliferating cell types of the plurality and wherein each proliferating cell type has an exogenous gene that when expressed produces an associated phenotype to the proliferating cell type which alters proliferation of the proliferating cell type,
inducing expression of one or more of the exogenous genes, and
determining the control relative number of unique associated barcodes after a period of proliferation.

8. The method of claim 1 wherein the perturbation is accomplished by introduction of a candidate compound to the combination of the plurality of proliferating cell types.

9. The method of claim 1 wherein the perturbation is accomplished by introduction of a candidate drug compound to the combination of the plurality of proliferating cell types, wherein the candidate drug compound inhibits the associated phenotype.

10. The method of claim 1 wherein the perturbation is accomplished by inducing expression of a target gene within the combination of the plurality of proliferating cell types.

11. The method of claim 1 wherein the perturbation is accomplished by reducing expression of a target gene within the combination of the plurality of proliferating cell types.

12. The method of claim 1 wherein the relative number of unique associated barcodes is determined by sequencing of the genome of the plurality of proliferating cell types.

13. The method of claim 1 wherein the plurality of proliferating cell types is a plurality of yeast strains.

14. The method of claim 1 wherein the plurality of proliferating cell types is a plurality of bacterial strains.

15. The method of claim 1 wherein the plurality of proliferating cell types is a plurality of mammalian cell lines.

16. The method of claim 1 wherein the plurality of proliferating cell types is a plurality of human cell lines.

17. The method of claim 1 wherein the plurality of proliferating cell types is a plurality of neuronal cell lines.

18. The method of claim 1 wherein the plurality of proliferating cell types is a plurality of human neuronal cell lines.

19. The method of claim 1 wherein the proliferating cell type is a proliferating organism or cell line.

20. The method of claim 1 wherein the proliferating cell type is a member selected from the group consisting of HEK 293, Chinese Hamster Ovary cells, HEK 293F, HEK 293H, HEK 293A, HEK 293 FT, HEK293T, CHO DG44, CHO-S, CHO-DXB11, Expi293F, ExpiCHO-S, T-Rex, Hela, MCF7, COS7, NIH 3T3, U2OS, A375, A549, N2A, PGP1 iPS, BHK, Hap1, Jurkat, and N0.

21. The method of claim 1 wherein the exogenous gene is a member selected from the group consisting of Abeta, Androgen receptor (AR), a-syn A30P, a-syn A53T, a-syn WT, ataxin1, Ataxin1 [Q84], ataxin3, ATXN7, C9orf72 GA100, C9orf72 GA200, C9orf72 GA50, C9orf72 GR100, C9orf72 GR50, C9orf72 PR50, CHOPS M8, CHOPS Wt, EWSR1, EWSR1c1655t, EWSR1g1532c, EWSR1g1750a, FUS WT, FUS-P525L, hnRNPA1 WT, hnRNPA1D262V, hnRNPA2B1 D290V, hnRNPA2B1WT, htt72Q, htt103Q, Htt46Q, PABPN1, SOD1 A4V, SOD1 G85R, SOD1 G93A, SOD1 WT, TAF15, TAF15c1222t, TAF15g1172a, Tau, TDP43, TDP-43 G294A, TDP-43 M337V, TDP-43 Q331K, UBQLN2, CHMP2B, PABPN1, ARX, SOX3, RUNX2, ZIC2, PHOX2B, HOXD13, HOXA13, FOXL2, ATXN2, CACNA1A, PrP, and TBP.

22. The method of claim 1 wherein introducing the perturbation comprises administering Lovastatin or Celestrol.

23. The method of claim 1 wherein introducing the perturbation comprises providing a Cas protein and a guide RNA targeting an endogenous gene.

\* \* \* \* \*

```
                           SEQUENCE LISTING

<160> NUMBER OF SEQ ID NOS: 14

<210> SEQ ID NO 1
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(32)
<223> OTHER INFORMATION: a, c, t, g, unknown or other

<400> SEQUENCE: 1
ctttccctac acgacgctct tccgatctnn nncacagttt aaactaatat acacatttta      60
cgg                                                                   63

<210> SEQ ID NO 2
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(32)
<223> OTHER INFORMATION: a, c, t, g, unknown or other

<400> SEQUENCE: 2
ctttccctac acgacgctct tccgatctnn nngtgttttt aaactaatat acacatttta      60
cgg                                                                   63

<210> SEQ ID NO 3
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(32)
<223> OTHER INFORMATION: a, c, t, g, unknown or other

<400> SEQUENCE: 3
ctttccctac acgacgctct tccgatctnn nntcttgttt aaactaatat acacatttta      60
cgg                                                                   63

<210> SEQ ID NO 4
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
```

```
<221> NAME/KEY: modified_base
<222> LOCATION: (29)..(32)
<223> OTHER INFORMATION: a, c, t, g, unknown or other

<400> SEQUENCE: 4
ctttccctac acgacgctct tccgatctnn nnagctcttt aaactaatat acacatttta        60
cgg                                                                     63

<210> SEQ ID NO 5
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggagttcaga cgtgtgctct tccgatctaa cgccgccatc cagtttaaac gag              53

<210> SEQ ID NO 6
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aaaaaccccg gattctagaa aaatggatgt attcatgaaa ggactt                      46

<210> SEQ ID NO 7
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aagaaattcg catcgatttt tcgcaccagt tcggcacatg accattatta ggcttcaggt        60
tcgtagtctt ga                                                           72

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tggtcatgtg ccgaactgg                                                    19

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgaaacttct ccgcagtgaa ag                                                22

<210> SEQ ID NO 10
```

```
<211> LENGTH: 606
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
cctctatact ttaacgtcaa ggagaaaaaa ccccggattc tagaactagt gtaggatcga      60
tgcgaatttc ttatgattta tgatttttat tattaaataa gttataaaaa aaataagtgt     120
atacaaattt taaagtgact cttaggtttt aaaacgaaaa ttcttaagac ataaaaaaca     180
aaaaaagcac caccgactcg gtgccacttt ttcaagttga taacggacta gccttatttt     240
aacttgctat ttctagctct aaaaccgaga cgcattaatc gtctcggatc atttatcttt     300
cactgcggag aagtttcgaa cgccgaaaca tgcgcaccaa ctttcacttc tacagcgttt     360
gaccaaaatc ttttgaacat aacattgtag ggtgtgaaaa aatgcgcacc tttaccgcta     420
gcccaagagg gcactacaaa atctagagtt gtacttcaaa cgtacatgta atcccttgta     480
tatactcgaa agaaaacatc aagtttctgt ataaatatga gtgaaagcat aatcatacat     540
tatcttttca aagacgcgtg tacgcatgta acattatact gaaaaccttg cttgagaagg     600
ttttgg                                                               606

<210> SEQ ID NO 11
<211> LENGTH: 426
<212> TYPE: DNA
<213> ORGANISM: Homo sapiens

<400> SEQUENCE: 11
atggatgtat tcatgaaagg actttcaaag gccaaggagg gagttgtggc tgctgctgag      60
aaaaccaaac agggtgtggc agaagcagca ggaaagacaa agagggtgt  tctctatgta     120 ggctccaaaa ccaaggaggg agtggtgcat ggtgtgacaa cagtggctga aagaccaaa      180 gagcaagtga caaatgttgg aggagcagtg gtgacgggtg tgacagcagt agcccagaag     240
acagtggagg gagcagggag cattgcagca gccactggct ttgtcaaaaa ggaccagttg     300
ggcaagaatg aagaaggagc cccacaggaa ggaattctgg aagatatgcc tgtggatcct     360
gacaatgagg cttatgaaat gccttctgag gaagggtatc aagactacga acctgaagcc     420
taataa                                                               426

<210> SEQ ID NO 12
<211> LENGTH: 5930
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gacgctcgaa ggctttaatt tgcggccggt acccaattcg ccctatagtg agtcgtatta      60
cgcgcgctca ctggccgtcg ttttacaacg tcgtgactgg gaaaaccctg gcgttaccca     120
acttaatcgc cttgcagcac atccccctt  cgccagctgg cgtaatagcg aagaggcccg     180
caccgatcgc ccttcccaac agttgcgcag cctgaatggc gaatggcgcg acgcgccctg     240
tagcggcgca ttaagcgcgg cgggtgtggt ggttacgcgc agcgtgaccg ctacacttgc     300
cagcgcccta gcgcccgctc ctttcgcttt cttcccttcc tttctcgcca cgttcgccgg     360
ctttccccgt caagctctaa atcgggggct ccctttaggg ttccgattta gtgctttacg     420
```

```
gcacctcgac cccaaaaaac ttgattaggg tgatggttca cgtagtgggc catcgccctg    480
atagacggtt tttcgcccct tgacgttgga gtccacgttc tttaatagtg gactcttgtt    540
ccaaactgga acaacactca accctatctc ggtctattct tttgatttat aagggatttt    600
gccgatttcg gcctattggt taaaaaatga gctgatttaa caaaaattta acgcgaattt    660
taacaaaata ttaacgttta caatttcctg atgcggtatt ttctccttac gcatctgtgc    720
ggtatttcac accgcataga tccgtcgagt tcaagagaaa aaaaagaaa aagcaaaaag    780 aaaaaaggaa agcgcgcctc gttcagaatg acacgtatag aatgatgcat taccttgtca    840
tcttcagtat catactgttc gtatacatac ttactgacat tcataggtat acatatatac    900
acatgtatat atatcgtatg ctgcagcttt aaataatcgg tgtcactaca taagaacacc    960
tttggtggag ggaacatcgt tggtaccatt gggcgaggtg gcttctctta tggcaaccgc   1020
aagagccttg aacgcactct cactacggtg atgatcattc ttgcctcgca gacaatcaac   1080
gtggagggta attctgctag cctctgcaaa gctttcaaga aaatgcggga tcatctcgca   1140
agagagatct cctactttct ccctttgcaa accaagttcg acaactgcgt acggcctgtt   1200
cgaaagatct accaccgctc tggaaagtgc ctcatccaaa ggcgcaaatc ctgatccaaa   1260 ccttttttact ccacgcgcca gtagggcctc tttaaaagct tgaccgagag caatcccgca   1320
gtcttcagtg gtgtgatggt cgtctatgtg taagtcacca atgcactcaa cgattagcga   1380
ccagccggaa tgcttggcca gagcatgtat catatggtcc agaaaccta cctgtgtg    1440 gacgttaatc acttgcgatt gtgtggcctg ttctgctact gcttctgcct cttttttctgg   1500 gaagatcgag tgctctatcg ctaggggacc acccttaaaa gagatcgcaa tctgaatctt   1560
ggtttcattt gtaatacgct ttactagggc tttctgctct gtcatctttg ccttcgttta   1620
tcttgcctgc tcattttta gtatattctt cgaagaaatc acattacttt ataaatgta   1680 taattcatta tgtgataatg ccaatcgcta agaaaaaaaa agagtcatcc gctaggggaa   1740 aaaaaaaat gaaaatcatt accgaggcat aaaaaaatat agagtgtact agaggaggcc   1800
aagagtaata gaaaagaaa attgcgggaa aggactgtgt tatgacttcc ctgactaatg   1860
ccgtgttcaa acgatacctg gcagtgactc ctagcgctca ccaagctctt aaaacgggaa   1920
tttatggtgc actctcagta caatctgctc tgatgccgca tagttaagcc agccccgaca   1980
cccgccaaca cgcgctgacg cgccctgacg ggcttgtctg ctcccggcat ccgcttacag   2040
acaagctgtg accgtctccg ggagctgcat gtgtcagagg ttttcaccgt catcaccgaa   2100
acgcgcgaga cgaaagggcc tcgtgatacg cctatttta taggttaatg tcatgataat   2160
aatggtttct taggacggat cgcttgcctg taacttacac gcgcctcgta tcttttaatg   2220
atggaataat ttgggaattt actctgtgtt tatttatttt tatgttttgt atttggattt   2280
tagaaagtaa ataaagaagg tagaagagtt acggaatgaa gaaaaaaaa taaacaaagg   2340 tttaaaaaat ttcaacaaaa agcgtacttt acatatatat ttattagaca agaaaagcag   2400
attaaataga tatacattcg attaacgata agtaaaatgt aaaatcacag gattttcgtg   2460
tgtggtcttc tacacagaca agatgaaaca attcggcatt aatacctgag agcaggaaga   2520
gcaagataaa aggtagtatt tgttggcgat cccctagag tcttttacat cttcggaaaa   2580
caaaaactat ttttcttta atttctttt ttactttcta tttttaattt atatatttat   2640
attaaaaaat ttaaattata attatttta tagcacgtga tgaaaggac ccaggtggca   2700 cttttcgggg aaatgtgcgc ggaacccta tttgtttatt tttctaaata cattcaaata   2760
```

-continued

```
tgtatccgct catgagacaa taaccctgat aaatgcttca ataatattga aaaggaaga      2820 gtatgagtat tcaacatttc cgtgtcgccc ttattccctt ttttgcggca ttttgccttc     2880 ctgttttgc tcacccagaa acgctggtga agtaaaaga tgctgaagat cagttgggtg      2940
cacgagtggg ttacatcgaa ctggatctca acagcggtaa gatccttgag agttttcgcc   3000
ccgaagaacg ttttccaatg atgagcactt ttaaagttct gctatgtggc gcggtattat    3060
cccgtattga cgccgggcaa gagcaactcg gtcgccgcat acactattct cagaatgact   3120
tggttgagta ctcaccagtc acagaaaagc atcttacgga tggcatgaca gtaagagaat   3180
tatgcagtgc tgccataacc atgagtgata acactgcggc caacttactt ctgacaacga   3240
tcggaggacc gaaggagcta accgcttttt tgcacaacat gggggatcat gtaactcgcc    3300
ttgatcgttg gaaccggag ctgaatgaag ccataccaaa cgacgagcgt gacaccacga    3360
tgcctgtagc aatggcaaca acgttgcgca aactattaac tggcgaacta cttactctag   3420
cttcccggca acaattaata gactggatgg aggcggataa agttgcagga ccacttctgc    3480
gctcggccct tccggctggc tggtttattg ctgataaatc tggagccggt gagcgtgggt   3540
ctcgcggtat cattgcagca ctggggccag atggtaagcc ctcccgtatc gtagttatct   3600
acacgacggg gagtcaggca actatggatg aacgaaatag acagatcgct gagataggtg    3660
cctcactgat taagcattgg taactgtcag accaagttta ctcatatata ctttagattg    3720
atttaaaact tcattttta tttaaaagga tctaggtgaa gatcctttt gataatctca      3780 tgaccaaaat cccttaacgt gagttttcgt tccactgagc gtcagacccc gtagaaaaga   3840
tcaaaggatc ttcttgagat cctttttttc tgcgcgtaat ctgctgcttg caaacaaaaa     3900
aaccaccgct accagcggtg gtttgtttgc cggatcaaga gctaccaact cttttttccga   3960 aggtaactgg cttcagcaga gcgcagatac caaatactgt ccttctagtg tagccgtagt   4020
taggccacca cttcaagaac tctgtagcac cgcctacata cctcgctctg ctaatcctgt   4080
taccagtggc tgctgccagt ggcgataagt cgtgtcttac cgggttggac tcaagacgat    4140
agttaccgga taaggcgcag cggtcgggct gaacggggg ttcgtgcaca cagcccagct    4200
tggagcgaac gacctacacc gaactgagat acctacagcg tgagctatga aaagcgcca     4260 cgcttcccga agggagaaag gcggacaggt atccggtaag cggcagggtc ggaacaggag   4320
agcgcacgag ggagcttcca ggggaaacg cctggtatct ttatagtcct gtcgggtttc    4380
gccacctctg acttgagcgt cgatttttgt gatgctcgtc agggggggcgg agcctatgga   4440 aaaacgccag caacgcggcc tttttacggt tcctggcctt ttgctggcct tttgctcaca    4500
tgttctttcc tgcgttatcc cctgattctg tggataaccg tattaccgcc tttgagtgag    4560
ctgataccgc tcgccgcagc cgaacgaccg agcgcagcga gtcagtgagc gaggaagcgg    4620
aagagcgccc aatacgcaaa ccgcctctcc ccgcgcgttg gccgattcat taatgcagct    4680
ggcacgacag gtttcccgac tggaaagcgg gcagtgagcg caacgcaatt aatgtgagtt    4740
acctcactca ttaggcaccc caggctttac actttatgct tccggctcct atgttgtgtg    4800
gaattgtgag cggataacaa tttcacacag gaaacagcta tgaccatgat tacgccaagc    4860
gcgcaattaa ccctcactaa agggaacaaa agctggagct ctagtacgga ttagaagccg   4920
ccgagcgggc gacagccctc cgacggaaga ctctcctccg tgcgtcctcg tcttcaccgg    4980
tcgcgttcct gaaacgcaga gtgtgcctcgc gccgcactgc tccgaacaat aaagattcta   5040
caatactagc ttttatggtt atgaagagga aaaattggca gtaacctggc cccacaaacc    5100
ttcaaattaa cgaatcaaat taacaaccat aggatgataa tgcgattagt ttttttagcct    5160
```

```
tatttctggg gtaattaatc agcgaagcga tgatttttga tctattaaca gatatataaa    5220
tggaaaagct gcataaccac tttaactaat actttcaaca ttttcagttt gtattacttc    5280
ttattcaaat gtcataaaag tatcaacaaa aaattgttaa tatacctcta tactttaacg    5340
tcaaggagaa aaaccccgg attctagaac tagtgtagga tcgatgcgaa tttcttatga     5400
tttatgattt ttattattaa ataagttata aaaaaataa gtgtatacaa attttaaagt     5460
gactcttagg ttttaaaacg aaaattctta agacataaaa aacaaaaaaa gcaccaccga    5520
ctcggtgcca cttttcaag ttgataacgg actagcctta ttttaacttg ctatttctag     5580
ctctaaaacc gagacgcatt aatcgtctcg gatcatttat ctttcactgc ggagaagttt    5640
cgaacgccga acatgcgca ccaactttca cttctacagc gtttgaccaa atctttttga     5700
acataacatt gtagggtgtg aaaaaatgcg cacctttacc gctagcccaa gagggcacta    5760
caaaatctag agttgtactt caaacgtaca tgtaatccct tgtatatact cgaaagaaaa    5820
catcaagttt ctgtataaat atgagtgaaa gcataatcat acattatctt ttcaaagacg    5880
cgtgtacgca tgtaacatta tactgaaaac cttgcttgag aaggttttgg                5930

<210> SEQ ID NO 13
<211> LENGTH: 6375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gacgctcgaa ggctttaatt tgcggccggt acccaattcg ccctatagtg agtcgtatta      60
cgcgcgctca ctggccgtcg ttttacaacg tcgtgactgg gaaaaccctg gcgttaccca    120
acttaatcgc cttgcagcac atccccctt cgccagctgg cgtaatagcg aagaggcccg     180
caccgatcgc ccttcccaac agttgcgcag cctgaatggc gaatggcgcg acgcgccctg    240
tagcggcgca ttaagcgcgg cgggtgtggt ggttacgcgc agcgtgaccg ctacacttgc    300
cagcgcccta gcgcccgctc ctttcgcttt cttcccttcc tttctcgcca cgttcgccgg    360
ctttccccgt caagctctaa atcggggggct ccctttaggg ttccgattta gtgctttacg   420
gcacctcgac cccaaaaaac ttgattaggg tgatggttca cgtagtgggc catcgccctg    480
atagacggtt tttcgccctt tgacgttgga gtccacgttc tttaatagtg gactcttgtt    540
ccaaactgga acaacactca acctatctc ggtctattct tttgatttat aagggatttt     600
gccgatttcg gcctattggt taaaaatga gctgatttaa caaaaattta acgcgaattt     660
taacaaaata ttaacgttta caatttcctg atgcggtatt ttctccttac gcatctgtgc    720 ggtattcac accgcataga tccgtcgagt tcaagagaaa aaaaagaaa aagcaaaaag      780 aaaaaggaa agcgcgcctc gttcagaatg acacgtatag aatgatgcat taccttgtca    840
tcttcagtat catactgttc gtatacatac ttactgacat tcataggtat acatatatac    900
acatgtatat atatcgtatg ctgcagcttt aaataatcgg tgtcactaca taagaacacc    960
tttggtggag ggaacatcgt tggtaccatt gggcgaggtg gcttctctta tggcaaccgc   1020
aagagccttg aacgcactct cactacggtg atgatcattc ttgcctcgca gacaatcaac   1080
gtggagggta attctgctag cctctgcaaa gctttcaaga aaatgcggga tcatctcgca   1140
agagagatct cctactttct cccttttgcaa accaagttcg acaactgcgt acggcctgtt   1200
cgaaagatct accaccgctc tggaaagtgc ctcatccaaa ggcgcaaatc ctgatccaaa    1260
```

```
ccttttttact ccacgcgcca gtagggcctc tttaaaagct tgaccgagag caatcccgca    1320
gtcttcagtg gtgtgatggt cgtctatgtg taagtcacca atgcactcaa cgattagcga    1380
ccagccggaa tgcttggcca gagcatgtat catatggtcc agaaaccctaa tacctgtgtg   1440 gacgttaatc acttgcgatt gtgtggcctg ttctgctact gcttctgcct ctttttctgg    1500
gaagatcgag tgctctatcg ctaggggacc acccttttaaa gagatcgcaa tctgaatctt   1560
ggtttcattt gtaatacgct ttactagggc tttctgctct gtcatctttg ccttcgttta    1620
tcttgcctgc tcattttttaa gtatattctt cgaagaaatc acattacttt atataatgta   1680
taattcatta tgtgataatg ccaatcgcta agaaaaaaaa agagtcatcc gctaggggaa    1740
aaaaaaaaat gaaatcatt accgaggcat aaaaaaatat agagtgtact agaggaggcc     1800
aagagtaata gaaaagaaa attgcgggaa aggactgtgt tatgacttcc ctgactaatg     1860
ccgtgttcaa acgatacctg gcagtgactc ctagcgctca ccaagctctt aaaacgggaa    1920
tttatggtgc actctcagta caatctgctc tgatgccgca tagttaagcc agccccgaca    1980
cccgccaaca cgcgctgacg cgccctgacg ggcttgtctg ctcccggcat ccgcttacag    2040
acaagctgtg accgtctccg ggagctgcat gtgtcagagg ttttcaccgt catcaccgaa    2100
acgcgcgaga cgaaagggcc tcgtgatacg cctattttta taggttaatg tcatgataat    2160
aatggtttct taggacggat cgcttgcctg taacttacac gcgcctcgta tcttttaatg    2220
atggaataat ttgggaattt actctgtgtt tatttatttt tatgttttgt atttggattt    2280
tagaaagtaa ataagaagg tagaagagtt acggaatgaa gaaaaaaaaa taaacaaagg     2340
tttaaaaaat ttcaacaaaa agcgtacttt acatatatat ttattagaca agaaaagcag    2400
attaaataga tatacattcg attaacgata agtaaaatgt aaaatcacag gattttcgtg    2460
tgtggtcttc tacacagaca agatgaaaca attcggcatt aatacctgag agcaggaaga    2520
gcaagataaa aggtagtatt tgttggcgat cccctagag tcttttacat cttcggaaaa     2580
caaaaactat ttttctttta atttcttttt ttactttcta tttttaatt atatatttat     2640 attaaaaat ttaaattata attatttta tagcacgtga tgaaaaggac ccaggtggca      2700
cttttcgggg aaatgtgcgc ggaacccta tttgtttatt tttctaaata cattcaaata    2760
tgtatccgct catgagacaa taaccctgat aaatgcttca ataatattga aaaaggaaga    2820
gtatgagtat tcaacatttc cgtgtcgccc ttattccctt ttttgcggca ttttgccttc    2880 ctgttttgc tcacccagaa acgctggtga agtaaaaga tgctgaagat cagttgggtg     2940
cacgagtggg ttacatcgaa ctggatctca acagcggtaa gatccttgag agttttcgcc    3000
ccgaagaacg ttttccaatg atgagcactt taaagttct gctatgtggc gcggtattat     3060
cccgtattga cgccgggcaa gagcaactcg gtcgccgcat acactattct cagaatgact   3120
tggttgagta ctcaccagtc acagaaaagc atcttacgga tggcatgaca gtaagagaat   3180
tatgcagtgc tgccataacc atgagtgata acactgcggc caacttactt ctgacaacga    3240
tcggaggacc gaaggagcta accgcttttt tgcacaacat gggggatcat gtaactcgcc    3300
ttgatcgttg ggaaccggag ctgaatgaag ccataccaaa cgacgagcgt gacaccacga    3360
tgcctgtagc aatggcaaca acgttgcgca aactattaac tggcgaacta cttactctag    3420
cttcccggca acaattaata gactggatgg aggcggataa agttgcagga ccacttctgc    3480
gctcggccct tccggctggc tggttttattg ctgataaatc tggagccggt gagcgtgggt    3540
ctcgcggtat cattgcagca ctggggccag atggtaagcc ctcccgtatc gtagttatct    3600
```

```
acacgacggg gagtcaggca actatggatg aacgaaatag acagatcgct gagataggtg    3660
cctcactgat taagcattgg taactgtcag accaagttta ctcatatata ctttagattg    3720
atttaaaact tcatttttaa tttaaaagga tctaggtgaa gatccttttt gataatctca    3780
tgaccaaaat cccttaacgt gagttttcgt tccactgagc gtcagacccc gtagaaaaga    3840
tcaaaggatc ttcttgagat cctttttttc tgcgcgtaat ctgctgcttg caaacaaaaa    3900
aaccaccgct accagcggtg gtttgtttgc cggatcaaga gctaccaact cttttccga    3960 aggtaactgg cttcagcaga gcgcagatac caaatactgt ccttctagtg tagccgtagt    4020
taggccacca cttcaagaac tctgtagcac cgcctacata cctcgctctg ctaatcctgt    4080
taccagtggc tgctgccagt ggcgataagt cgtgtcttac cgggttggac tcaagacgat    4140
agttaccgga taaggcgcag cggtcgggct gaacggggg ttcgtgcaca cagcccagct    4200
tggagcgaac gacctacacc gaactgagat acctacagcg tgagctatga gaaagcgcca    4260
cgcttcccga agggagaaag gcggacaggt atccggtaag cggcagggtc ggaacaggag    4320
agcgcacgag ggagcttcca gggggaaacg cctggtatct ttatagtcct gtcgggtttc    4380
gccacctctg acttgagcgt cgatttttgt gatgctcgtc agggggcgg agcctatgga    4440 aaaacgccag caacgcggcc tttttacggt tcctggcctt ttgctggcct tttgctcaca    4500
tgttctttcc tgcgttatcc cctgattctg tggataaccg tattaccgcc tttgagtgag    4560
ctgataccgc tcgccgcagc cgaacgaccg agcgcagcga gtcagtgagc gaggaagcgg    4620
aagagcgccc aatacgcaaa ccgcctctcc ccgcgcgttg gccgattcat taatgcagct    4680
ggcacgacag gtttcccgac tggaaagcgg gcagtgagcg caacgcaatt aatgtgagtt    4740
acctcactca ttaggcaccc caggctttac actttatgct tccggctcct atgttgtgtg    4800
gaattgtgag cggataacaa tttcacacag gaaacagcta tgaccatgat tacgccaagc    4860
gcgcaattaa ccctcactaa agggaacaaa agctggagct ctagtacgga ttagaagccg    4920
ccgagcgggc gacagccctc cgacggaaga ctctcctccg tgcgtcctcg tcttcaccgg    4980
tcgcgttcct gaaacgcaga tgtgcctcgc gccgcactgc tccgaacaat aaagattcta    5040
caatactagc ttttatggtt atgaagagga aaaattggca gtaacctggc cccacaaacc    5100
ttcaaattaa cgaatcaaat taacaaccat aggatgataa tgcgattagt ttttagcct    5160 tatttctggg gtaattaatc agcgaagcga tgatttttga tctattaaca gatatataaa    5220
tggaaaagct gcataaccac tttaactaat actttcaaca ttttcagttt gtattacttc    5280
ttattcaaat gtcataaaag tatcaacaaa aaattgttaa tatacctcta tactttaacg    5340
tcaaggagaa aaaccccgg attctagaaa aatggatgta ttcatgaaag gactttcaaa    5400
ggccaaggag ggagttgtgg ctgctgctga gaaaaccaaa cagggtgtgg cagaagcagc    5460
aggaaagaca aaagagggtg ttctctatgt aggctccaaa accaaggagg gagtggtgca    5520
tggtgtgaca acagtggctg agaagaccaa agagcaagtg acaaatgttg gaggagcagt    5580
ggtgacgggt gtgacagcag tagcccagaa gacagtggag ggagcaggga gcattgcagc    5640
agccactggc tttgtcaaaa aggaccagtt gggcaagaat gaagaaggag ccccacagga    5700
aggaattctg gaagatatgc ctgtggatcc tgacaatgag gcttatgaaa tgccttctga    5760
ggaagggtat caagactacg aacctgaagc ctaataatgg tcatgtgccg aactggtgcg    5820
aaaaatcgat gcgaatttct tatgattat gatttttatt attaaataag ttataaaaaa    5880
aataagtgta tacaaatttt aaagtgactc ttaggttta aaacgaaaat tcttaagaca    5940
taaaaaacaa aaaaagcacc accgactcgg tgccacttt tcaagttgat aacggactag    6000
```

```
ccttatttta acttgctatt tctagctcta aaaccgagac gcattaatcg tctcggatca      6060
tttatctttc actgcggaga agtttcgaac gccgaaacat gcgcaccaac tttcacttct      6120
acagcgtttg accaaaatct tttgaacata acattgtagg gtgtgaaaaa atgcgcacct      6180
ttaccgctag cccaagaggg cactacaaaa tctagagttg tacttcaaac gtacatgtaa      6240
tcccttgtat atactcgaaa gaaaacatca agtttctgta taaatatgag tgaaagcata      6300
atcatacatt atcttttcaa agacgcgtgt acgcatgtaa cattatactg aaaaccttgc      6360
ttgagaaggt tttgg                                                      6375

<210> SEQ ID NO 14
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gttttagagc tagaaatagc aagttaaaat aaggctagtc cgttatcaac ttgaaaaagt       60
ggcaccgagt cggtgctttt ttt                                              83
```